(12) United States Patent
Dininno et al.

(10) Patent No.: US 6,284,753 B2
(45) Date of Patent: *Sep. 4, 2001

(54) CARBAPENEM ANTIBACTERIAL COMPOUNDS, COMPOSITIONS CONTAINING SUCH COMPOUNDS AND METHODS OF TREATMENT

(75) Inventors: Frank P. Dininno, Old Bridge; Kevin D. Dykstra, West Milford, both of NJ (US)

(73) Assignee: Merck & Co., Inc., Rahway, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/317,790

(22) Filed: May 24, 1999

Related U.S. Application Data

(60) Provisional application No. 60/087,772, filed on Jun. 2, 1998.

(51) Int. Cl.[7] ..................... C07D 477/14; A61K 31/407; A61P 31/04
(52) U.S. Cl. ........................... 514/210.09; 540/302
(58) Field of Search ..................... 540/302; 514/210.09

(56) References Cited

U.S. PATENT DOCUMENTS

| | | | |
|---|---|---|---|
| 5,192,758 | 3/1993 | DiNinno et al. | 514/210 |
| 5,756,725 | * 5/1998 | Wilkening | 540/302 |

FOREIGN PATENT DOCUMENTS

| | | |
|---|---|---|
| 0 007 614 | 2/1980 | (EP) . |
| 0 072 014 | 2/1983 | (EP) . |

OTHER PUBLICATIONS

S. M. Schmitt Et Al., *J Antibiotics* 41(6): 780–787 (1988).
Michael E. Jung & Lyn A. Light, *Tet. Ltrs.*, 23(38): 3851–3854 (1982).
Keving D. Dykstra & Frank Dininno, *Tet. Ltrs.* 39: 1865–1868 (1998).

* cited by examiner

*Primary Examiner*—Mark L. Berch
(74) *Attorney, Agent, or Firm*—Sylvia A. Ayler; Mark R. Daniel

(57) ABSTRACT

The present invention relates to tricyclic carbapenem antibacterial agents wherein X is $CH_2$, $CHR^a$, $CHR^b$, $C=CHR^a$, $C=CHR^b$, O, S, SO, $SO_2$, CO, COO<OCO, $NR^a$, $NR^b$; and Z is trans-ethenediyl or ethynediyl. The compound is further substituted with various substituent groups including at least one cationic group.

The compounds are represented by formula I:

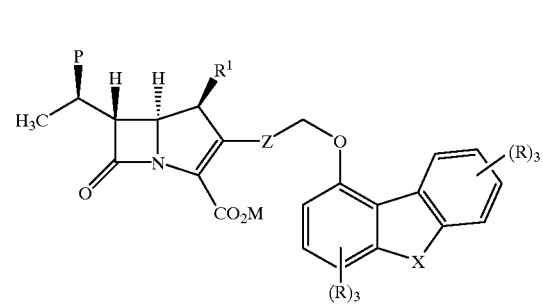

Pharmaceutical compositions and methods of use are also included.

28 Claims, No Drawings

CARBAPENEM ANTIBACTERIAL COMPOUNDS, COMPOSITIONS CONTAINING SUCH COMPOUNDS AND METHODS OF TREATMENT

This application claims the benefit of U.S. Provisional Application No. 60/087,772, filed Jun. 2, 1998.

BACKGROUND OF THE INVENTION

The present invention relates to carbapenem antibacterial agents in which the carbapenem nucleus is substituted at the 2-position with a condensed biaryl ring structure linked through a group —Z—CH$_2$—. Z represents an trans-ethenediyl or ethynediyl group. The dibenzopentacyclic ring structure is further substituted with various substituent groups including at least one cationic group.

The carbapenems of the present invention are useful against gram positive microorganisms, especially methicillin resistant Staphylococcus aureus (MRSA), methicillin resistant Staphylococcus epidermidis (MRSE), and methicillin resistant coagulase negative Staphylococci (MRCNS). The antibacterial compounds of the present invention thus comprise an important contribution to therapy for treating infections caused by these difficult to control pathogens.

There is an increasing need for agents effective against such pathogens (MRSA/MRCNS) which are at the same time relatively free from undesirable side effects.

SUMMARY OF THE INVENTION

The present invention relates to anti-MRSA carbapenem antibiotics containing aromatic based side-chains. The side-chain imparts MRS activity previously unassociated with the carbapenem skeleton.

The compounds of the invention are represented by formula I:

or a pharmaceutically acceptable salt thereof, wherein:

R$^1$ represents H or methyl;

CO$_2$M represents a carboxylic acid, a carboxylate anion, a pharmaceutically acceptable ester group or a carboxylic acid protected by a protecting group;

P represents hydrogen, hydroxyl, F, or hydroxyl protected by a hydroxyl-protecting group;

X represents absent, CH$_2$, CHR$^a$, CHR$^b$, C=CHR$^a$, C=CHR$^b$, O, S, SO, SO$_2$, CO, COO, OCO, NR$^a$, NR$^b$, with the proviso that only one R$^a$ and/or one R$^b$ may be present at any one time, the remaining ring positions being substituted with hydrogen;

Z represents trans-ethenediyl or ethynediyl;

each R is independently selected from: —R*; —Q; hydrogen; halo; —CN; —NO$_2$; —NR$^a$R$^b$; —OR$^c$; —SR$^c$; —C(O)NR$^a$R$^b$; —C(O)OR$^h$; —S(O)R$^c$; —SO$_2$R$^c$; —SO$_2$NR$^a$R$^b$; —NR$^a$SO$_2$R$^b$; —C(O)R$^a$; —OC(O)R$^a$; —OC(O)NR$^a$R$^b$; —NR$^a$C(O)NR$^b$R$^c$; —NR$^a$CO$_2$R$^h$; —OCO$_2$R$^h$; —NR$^a$C(O)R$^b$; —C$_{1-6}$ straight- or branched-chain alkyl, unsubstituted or substituted with one to four R$^d$ groups; and —C$_{3-7}$ cycloalkyl, unsubstituted or substituted with one to four R$^d$ groups;

each R$^a$, R$^b$ and R$^c$ independently represents hydrogen, —R*, —C$_{1-6}$ straight- or branched-chain alkyl, unsubstituted or substituted with one to four R$^d$ groups, or —C$_{3-7}$ cycloalkyl, unsubstituted or substituted with one to four R$^d$ groups;

or R$^a$ and R$^b$ taken together with any intervening atoms represent a 4–6 membered saturated ring optionally interrupted by one or more of O, S, NR$^c$, with R$^c$ as defined above, or —C(O)—, said ring being unsubstituted or substituted with one to four R$^i$ groups;

or R$^b$ and R$^c$ taken together with any intervening atoms represent a 4–6 membered saturated ring optionally interrupted by one to three of O, S, NR$^a$, with R$^a$ as defined above, or —C(O)—, said ring being unsubstituted or substituted with one to four R$^i$ groups;

each R$^d$ independently represents halo; —CN; —NO$_2$; —NR$^e$R$^f$; —OR$^g$; —SR$^g$; —CONR$^e$R$^f$; —COOR$^g$; —SOR$^g$; —SO$_2$R$^g$; —SO$_2$NR$^e$R$^f$; —NR$^e$SO$_2$R$^f$; —COR$^e$; —NR$^e$COR$^f$; —OCOR$^e$; —OCONR$^e$R$^f$; —NR$^e$CONR$^f$R$^g$; —NR$^e$CO$_2$R$^h$; —OCO$_2$R$^h$; —C(NR$^e$)NR$^f$R$^g$; —NR$^e$C(NH)NR$^f$R$^g$; —NR$^e$C(NR$^f$)R$^g$; —R* or —Q;

R$^e$, R$^f$ and R$^g$ represent hydrogen; —R*; —C$_{1-6}$ straight- or branched-chain alkyl, unsubstituted or substituted with one to four R$^i$ groups;

or R$^e$ and R$^f$ taken together with any intervening atoms represent a 4–6 membered saturated ring optionally interrupted by one to three of O, S, —C(O)— or NR$^g$ with R$^g$ as defined above, said ring being unsubstituted or substituted with one to four R$^i$ groups;

each R$^i$ independently represents halo; —CN; —NO$_2$; phenyl; —NHSO$_2$R$^h$; —OR$^h$, —SR$^h$; —N(R$^h$)$_2$; —N+(R$^h$)$_3$; —C(O)N(R$^h$)$_2$; —SO$_2$N(R$^h$)$_2$; heteroaryl; heteroarylium; —CO$_2$R$^h$; —C(O)R$^h$; —OCOR$^h$; —NHCOR$^h$; guanidinyl; carbamimidoyl or ureido;

each R$^h$ independently represents hydrogen, a —C$_{1-6}$ straight or branched-chain alkyl group, a —C$_3$-C$_6$ cycloalkyl group or phenyl, or when two R$^h$ groups are present, said R$^h$ groups may be taken in combination and represent a 4–6 membered saturated ring, optionally interrupted by one or two of O, S, SO$_2$, —C(O)—, NH and NCH$_3$;

Q is selected from the group consisting of:

wherein:
a and b are 1, 2 or 3;
L$^-$ is a pharmaceutically acceptable counterion;
α represents O, S or NR$^s$;

β, δ, λ, μ and σ represent CR$^t$, N or N$^+$R$^s$, provided that no more than one of β, δ, λ, μ and σ is N$^+$R$^s$;

R* is selected from the group consisting of:

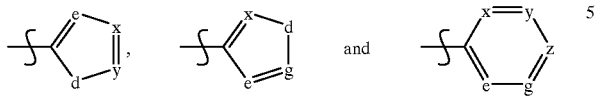

wherein:

d represents O, S or NR$^k$;

e, g, x, y and z represent CR$^m$, N or N$^+$R$^k$, provided that no more than one of e, g, x, y and z in any given structure represents N$^+$R$^k$;

R$^k$ represents hydrogen; —C$_{1-6}$ straight- or branched-chain alkyl, unsubstituted or substituted with one to four R$^i$ groups; or —(CH$_2$)$_n$Q where n=1, 2 or 3 and Q is as previously defined;

each R$^m$ independently represents a member selected from the group consisting of: hydrogen; halo; —CN; —NO$_2$; —NR$^n$R$^o$; —OR$^n$; —SR$^n$; —CONR$^n$R$^o$; —COOR$^h$; —SOR$^n$; —SO$_2$R$^n$; —SO$_2$NR$^n$R$^o$; —NR$^n$SO$_2$R$^o$; —COR$^n$; —NR$^n$COR$^o$; —OCOR$^n$; —OCONR$^n$R$^o$; —NR$^n$CO$_2$R$^h$; —NR$^n$CONR$^o$R$^h$; —OCO$_2$R$^h$; —CNR$^n$NR$^o$R$^h$; —NR$^n$CNHNR$^o$R$^h$; —NR$^n$C(NR$^o$)R$^h$; —C$_{1-6}$ straight- or branched-chain alkyl, unsubstituted or substituted with one to four R$^i$ groups; —C$_{3-7}$ cycloalkyl, unsubstituted or substituted with one to four R$^i$ groups; and —(CH$_2$)$_n$Q where n and Q are as defined above;

R$_n$ and R$_o$ represent hydrogen, phenyl; —C$_{1-6}$ straight- or branched-chain alkyl unsubstituted or substituted with one to four R$^i$ groups;

each R$^s$ independently represents hydrogen; phenyl or —C$_{1-6}$ straight- or branched-chain alkyl, unsubstituted or substituted with one to four R$^i$ groups;

each R$^t$ independently represents hydrogen; halo; phenyl; —CN; —NO$_2$; —NR$^u$R$^v$; —OR$^u$; —SR$^u$; —CONR$^u$R$^v$; —COOR$^h$; —SOR$^u$; —SO$_2$R$^u$; —SO$_2$NR$^u$R$^v$; —NR$^u$SO$_2$R$^v$; —COR$^u$; —NR$^u$COR$^v$; —OCOR$^u$; —OCONR$^u$R$^v$; —NR$^u$CO$_2$R$^v$; —NR$^u$CONR$^v$R$^v$; —OCO$_2$R$^v$; —C$_{1-6}$ straight- or branched-chain alkyl, unsubstituted or substituted with one to four R$^i$ groups;

R$^u$ and R$^v$ represent hydrogen or —C$_{1-6}$ straight- or branched-chain alkyl, unsubstituted or substituted with one to four R$^i$ groups;

or R$^u$ and R$^v$ together with any intervening atoms represent a 4–6 membered saturated ring optionally interrupted by one or more of O, S, NR$^w$ or —C(O)—, said ring being unsubstituted or substituted with one to four R$^i$ groups;

each R$^w$ independently represents hydrogen; —C$_{1-6}$ straight- or branched-chain alkyl, unsubstituted or substituted with one to four R$^i$ groups; C$_{3-6}$ cycloalkyl optionally substituted with one to four R$^i$ groups; phenyl optionally substituted with one to four R$^i$ groups, or heteroaryl optionally substituted with 1–4 R$^i$ groups;

or R$^h$ and R$^w$ taken together with any intervening atoms represent a 5–6 membered saturated ring, optionally interrupted by one or two of O, S, SO$_2$, NH or NCH$_3$;

R$^x$ represents hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, or a phenyl or heteroaryl group which is in turn optionally substituted with from one to four R$^i$ groups or with one to two C$_{1-3}$ straight- or branched-chain alkyl groups, said alkyl groups being unsubstituted or substituted with one to four R$^i$ groups;

R$^y$ and R$^z$ represent hydrogen; phenyl; —C$_{1-6}$ straight or branched chain alkyl, unsubstituted or substituted with one to four R$^i$ groups, and optionally interrupted by O, S, NR$^w$, N$^+$R$^h$R$^w$ or —C(O)—;

or R$^x$ and R$^y$ together with any intervening atoms represent a 4–6 membered saturated ring optionally interrupted by O, S, SO$_2$, NR$^w$, N$^+$R$^h$R$^w$ or —C(O)—, unsubstituted or substituted with 1–4 R$^i$ groups, and when R$^x$ and R$^y$ together represent a 4–6 membered ring as defined above, R$^z$ is as defined above or R$^z$ represents an additional saturated 4–6 membered ring fused to the ring represented by R$^x$ and R$^y$ taken together, optionally interrupted by O, S, NR$^w$ or —C(O)—, said rings being unsubstituted or substituted with one to four R$^i$ groups.

Pharmaceutical compositions and methods of treatment are also included herein.

DETAILED DESCRIPTION OF THE INVENTION

The invention is described herein in detail using the terms defined below unless otherwise specified.

Carboxylate anion refers to a negatively charged group —COO—.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to four substituent groups, selected from R$^d$ and R$^i$, as defined, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical, straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical, straight or branched, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole and oxazine. Additional nitrogen atoms may be present together with the first nitrogen and oxygen or sulfur, giving, e.g., thiadiazole. Examples include the following:

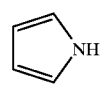 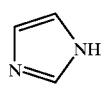 

pyrrole (pyrrolyl)   imidazole (imidazolyl)   thiazole (thiazolyl)

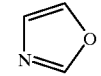 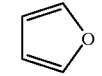 

oxazole (oxazolyl)   furan (furyl)   thiophene (thienyl)

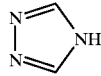 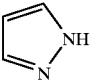 

triazole (triazolyl)   pyrazole (pyrazolyl)   isoxazole (isoxazolyl)

 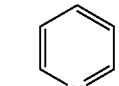 

isothiazole (isothiazolyl)   pyridine (pyridinyl)   pyrazine (pyrazinyl)

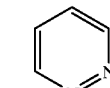 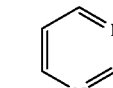 

pyridazine (pyridazinyl)   pyrimidine (pyrimidinyl)   triazine (triazinyl)

Heteroarylium refers to heteroaryl groups bearing a quaternary nitrogen atom and thus a positive charge. Examples include the following:

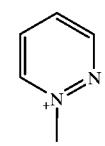 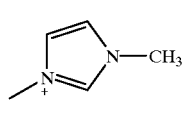 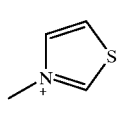

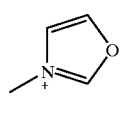 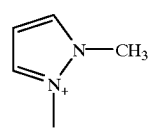 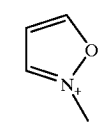

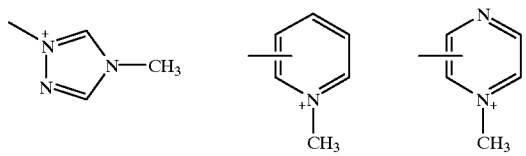

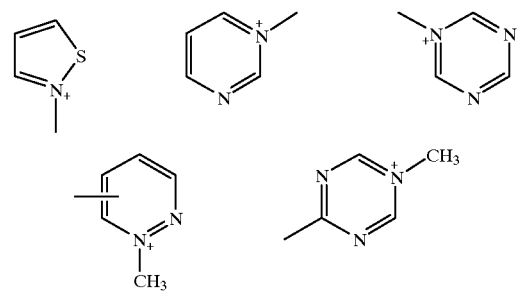

When a charge is shown on a particular nitrogen atom in a ring which contains one or more additional nitrogen atoms, it is understood that the charge may reside on a different nitrogen atom in the ring by virtue of charge resonance that occurs.

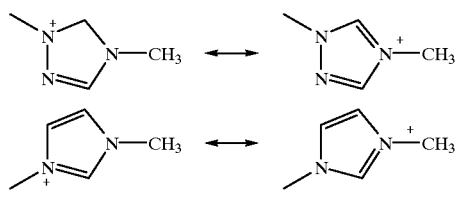

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e. g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Halogen and "halo" refer to bromine, chlorine, fluorine and iodine.

Alkoxy refers to $C_1$–$C_4$ alkyl-O—, with the alkyl group optionally substituted as described herein.

When a group is termed "substituted", unless otherwise indicated, this means that the group contains from 1 to 4 substituents thereon. With respect to R, $R^a$, $R^b$ and $R^c$, the substituents available on alkyl groups are selected from the values of $R^d$. Many of the variable groups are optionally substituted with up to four $R^i$ groups. With respect to $R^e$, $R^f$ and $R^g$, when these variables represent substituted alkyl, the substituents available thereon are selected from the values of $R^i$.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

When an alkyl group is "interrupted by" 1 or more moieties, such as O, S, N, —C(O)— and the like, this includes alkyl groups which are terminated by the moiety or moieties, as well as alkyl groups that are interrupted or terminated by combinations of such groups. Thus for example, —C(O)O—, —OC(O)—, —C(O)NR$^8$— and similar such moieties are included. Examples of alkyl groups terminated by the moiety or moieties are as follows: —O—C$_{1-6}$ alkyl, —C$_{1-6}$ alkyl-O—, —C$_{1-6}$ alkyl-OC(O)—, —O—C$_{1-6}$ alkyl-S— and the like. Obviously other moieties are included in accordance with the general description contained herein.

In some of the carbapenem compounds of the present invention, M is a readily removable carboxyl protecting group, and/or P represents a hydroxyl which is protected by a hydroxyl-protecting group. Such conventional protecting groups consist of known groups which are used to protectively block the hydroxyl or carboxyl group during the synthesis procedures described herein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of carboxyl protecting groups include allyl, benzhydryl, 2-naphthylmethyl, benzyl, silyl such as t-butyldimethylsilyl (TBS), phenacyl, p-methoxybenzyl, o-nitrobenzyl, p-methoxyphenyl, p-nitrobenzyl, 4-pyridylmethyl and t-butyl.

Examples of suitable hydroxyl protecting groups include triethylsilyl (TES), t-butyldimethylsilyl (TBS), t-butyldiphenylsilyl (DPTBS), o-nitrobenzyloxycarbonyl, p-nitrobenzyloxycarbonyl, benzyloxycarbonyl, allyloxycarbonyl, t-butyloxycarbonyl, 2,2,2-trichloroethyloxycarbonyl and the like.

The carbapenem compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist. i.e., those which are substantially non-toxic and which may favorably affect the pharmacokinetic properties of said compounds, such as palatability, absorption, distribution, metabolism and excretion. Other factors, more practical in nature, which are also important in the selection, are cost of the raw materials, ease of crystallization, yield, stability, solubility, hygroscopicity and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

With respect to —CO$_2$M, which is attached to the carbapenem nucleus at position 3, this represents a carboxylic acid group (M represents H), a carboxylate anion (M represents a negative charge), a pharmaceutically acceptable ester (M represents an ester forming group) or a carboxylic acid protected by a protecting group (M represents a carboxyl protecting group). The pharmaceutically acceptable salts referred to above may take the form —COOM, where M is a negative charge, which is balanced by a counterion, e.g., an alkali metal cation such as sodium or potassium. Other pharmaceutically acceptable counterions may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above also include acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The pharmaceutically acceptable esters are such as would be readily apparent to a medicinal chemist, and include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947. These are also referred to as "biolabile esters".

Biolabile esters are biologically hydrolizable, and may be suitable for oral administration, due to good absorption through the stomach or intenstinal mucosa, resistance to gastric acid degradation and other factors. Examples of biolabile esters include compounds in which M represents an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

L– can be present or absent as necessary to maintain the appropriate charge balance. When present, L– represents a pharmaceutically acceptable counterion. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when L- represents a specie with more than one negative charge, such as malonate, tartrate or ethylenediamine-tetraacetate (EDTA), an appropriate number of carbapenem molecules can be found in association therewith to maintain the overall charge balance and neutrality.

At least one of the R groups attached to the diphenylpentacyclic platform can optionally contain a positively charged moiety. Thus, it can include —R* or Q, or a moiety which in turn contains a positively charged group.

A subset of compounds of formula I which is of interest relates to those compounds where $CO_2M$ represents a carboxylate anion. Hence, M in this instance represents a negative charge which will be balanced by a positively charged group, such as in the positively charged R group. Likewise, if the positively charged R group contains more than one positive charge, a negatively charged counterion may be present which in combination with the carboxylate anion, provides overall charge neutrality.

Another subset of compounds of formula I which is of interest relates to compounds wherein one R represents a group which contains a positively charged moiety, and the remaining R groups are selected from hydrogen and $C_{1-6}$ straight or branched chain alkyl, unsubstituted or substituted with one to four $R^d$ groups. More particularly, this subset of interest includes compounds of formula Ia wherein one R represents a group containing a positively charged moiety and the remaining R groups are hydrogen.

With respect to the positively charged moiety or moieties that are contained in one or more R groups, it is preferred that from 1–3 positive charges be present, and most preferably two positive charges be present, balanced by the carboxylate anion and a negatively charged counterion.

Another subset of compounds which is of interest is represented by formula I wherein one R group represents a —$C_{1-6}$ straight or branched chain alkyl group, substituted with one to four $R^d$ groups, wherein one $R^d$ group represents —R* or Q. Hence, a positively charged moiety —R* or Q is attached to an alkyl group.

Another group of compounds of interest is represented by formula I wherein Q is selected from the group consisting of:

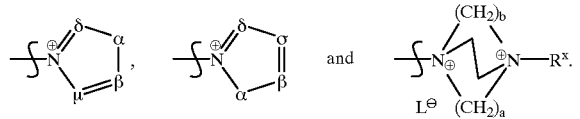

More particularly, the group of compounds which is of interest is represented by formula I wherein Q represents:

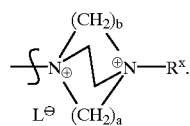

Within this subset of compounds, L-, a and b are as originally defined, and $R^x$ is as originally defined, and represents a member selected from the group consisting of: hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups.

Another group of compounds of interest is represented by formula I wherein Q represents —$N^+R^xR^yR^z$, wherein $R^x$, $R^y$ and $R^z$ are as originally defined.

Another group of compounds of interest is represented by formula I wherein one R* group is present and is selected from:

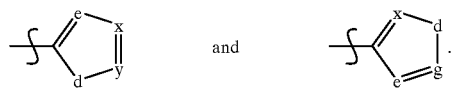

Within this subset, d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Another group of compounds of interest is represented by formula I wherein R is A—$(CH_2)_n$—Q, wherein A is O, S or $CH_2$ and n is 0–3 and Q is as originally defined.

Another group of compounds of interest is represented by formula I wherein Z is trans-CH=CH and all other variables are as originally described.

Another group of compounds of interest is represented by formula I wherein Z is —C≡C— and all other variables are as originally described.

Another group of compounds of interest is represented by formula I wherein X is $CH_2$, $CHR^a$, CO, O, $NR^a$, S, or $SO_2$; preferably $CHR^a$, CO, O or S;

A preferred subset of compounds of formula I which is of particular interest relates to compounds represented by formula Ia

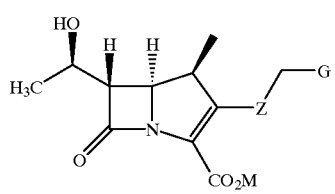

wherein G is:

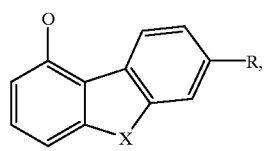

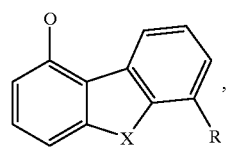

-continued

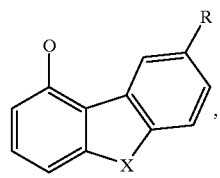
3

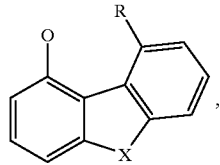
4

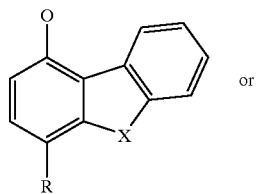
or
5

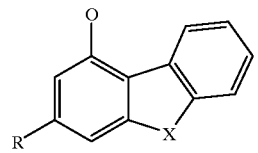
6 wherein:
Z is as originally described;
$CO_2M$ represents a carboxylate anion;
X represents $CH_2$, $CHR^a$, CO, O, S, or $NR^a$;
one R group contains at least one positively charged moiety, and the remaining R groups are selected from hydrogen and $C_{1-6}$ straight or branched chain alkyl, unsubstituted or substituted with one to four $R^d$ groups;
Rd is as originally defined;
$R^h$ represents hydrogen or a $C_{1-6}$ straight or branched chain alkyl group;
Q is selected from the group consisting of:

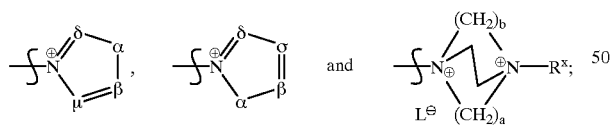

wherein
L–, a and b are as originally defined, and $R^x$ represents a member selected from the group consisting of: hydrogen or a $C_{1-8}$ straight- or branched-chain alkyl, optionally interrupted or terminated by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl or heteroaryl group being optionally substituted with from one to four $R^i$ groups or with one to two $C_{1-3}$ straight- or branched- chain alkyl groups, said alkyl groups being unsubstituted or substituted with one to four $R^i$ groups;

R* is selected from:

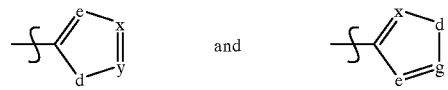

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Within this subset, all other variables are as originally defined with respect to formula I.

A preferred subset of compounds for formula Ia are realized when G is 1, 2 or 5, preferably 1 or 2.

Another preferred subset of compounds is represented by formula Ib:

Ib
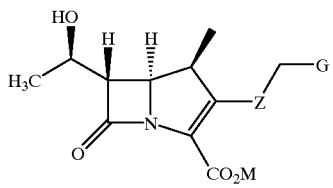

wherein G is:

7
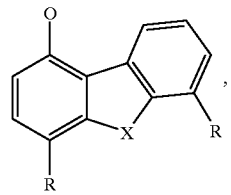

8
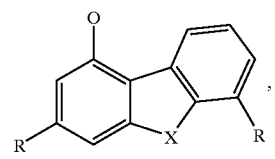

9
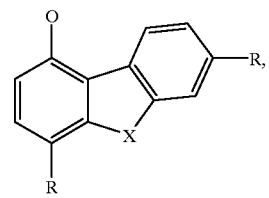

10
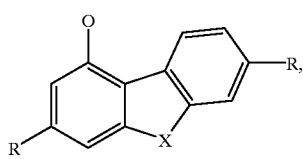

-continued

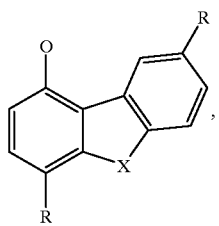

11

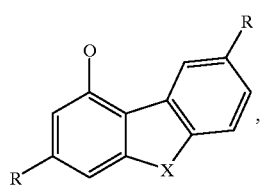

12

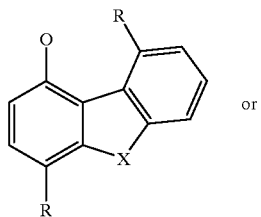

13 or

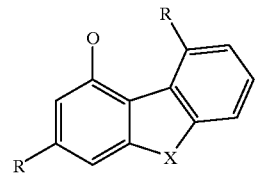

14 or a pharmaceutically acceptable salt thereof, wherein:
Z is as originally described;
$CO_2M$ represents a carboxylate anion;
one R group is attached to the condensed biaryl platform which contains a positively charged moiety, and the other R group is selected from hydrogen and $C_{1-6}$ straight or branched chain alkyl, unsubstituted or substituted with one to four $R^d$ groups;
$R^d$ is as originally defined;
Q is selected from the group consisting of:

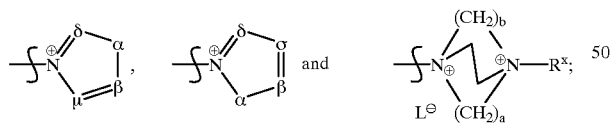

wherein
L—, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight- or branched-chain alkyl groups, said alkyl groups being unsubstituted or substituted with one to four $R^i$ groups;
$R^h$ represents hydrogen or a $C_{1-6}$ straight or branched chain alkyl group;
$R^w$ is as originally defined;
R* is selected from:

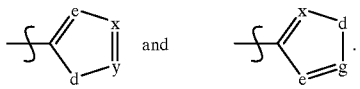

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen. Within this subset, all other variables are as originally defined with respect to formula I.

A preferred subset of compounds of formula Ib are realized when G is 7 or 8, preferably 7.

Another preferred subset of compounds is represented by formula Ic:

Ic

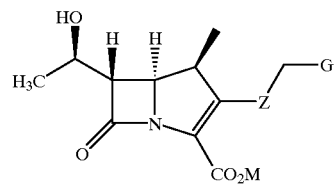

wherein G is:

1

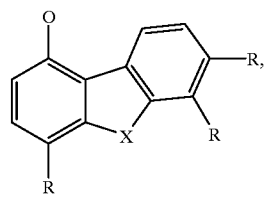

2

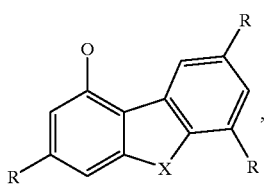

3

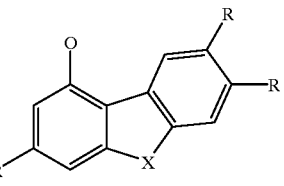

4

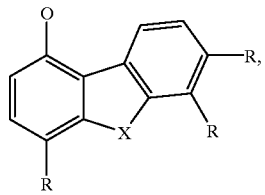

-continued

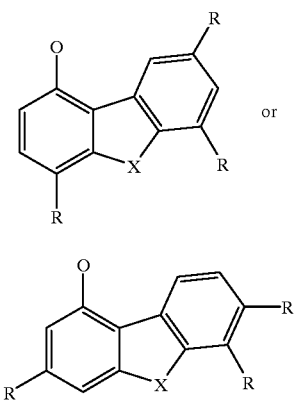

or a pharmaceutically acceptable salt thereof, wherein:
Z is as originally described;
$CO_2M$ represents a carboxylate anion;
one R group is attached to the condensed biaryl platform which contains a positively charged moiety, and the other R group is selected from hydrogen, halo and $C_{1-6}$ straight or branched chain alkyl, unsubstituted or substituted with one to four $R^d$ groups;
$R^d$ is as originally defined;
Q is selected from the group consisting of:

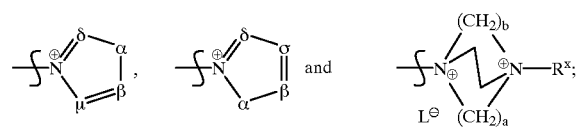

wherein
L−, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;
$R^h$ represents hydrogen or a $C_{1-6}$ straight or branched chain alkyl group;
$R^w$ is as originally defined;
R* is selected from:

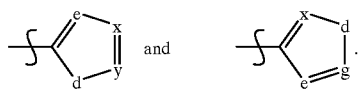

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen. Within this subset, all other variables are as originally defined with respect to formula I.

In particular, such compounds can be represented by formula Id:

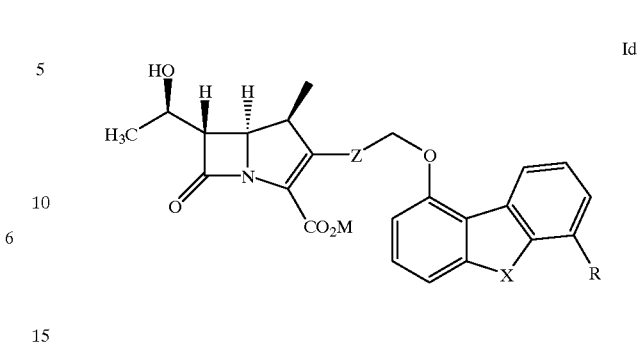

or a pharmaceutically acceptable salt thereof, wherein:

Z is as originally described;
R contains a positively charged moiety selected from the group consisting of: —R*, Q, A—$(CH_2)_n$—Q, and a $C_{1-6}$ straight or branched alkyl chain substituted with one $R^d$ group, wherein A is $CH_2$ and n is 2, or 3;
$R^d$ is independently selected —R* or Q;
Q is selected from the group consisting of:

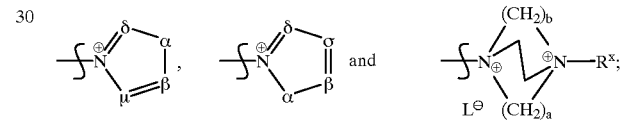

wherein
L−, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;
R* is selected from:

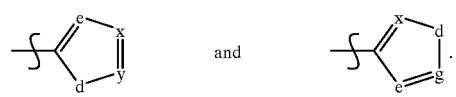

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

Likewise, such compounds can be represented by formula Ie:

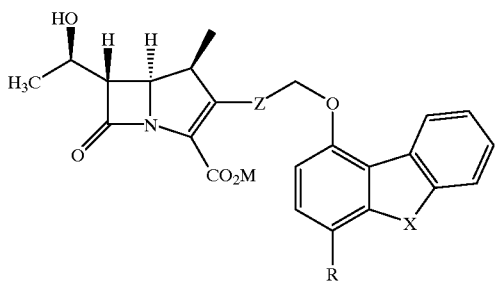

Ie or a pharmaceutically acceptable salt thereof, wherein:

R contains a positively charged moiety selected from the group consisting of: —R*, Q, A—(CH$_2$)$_n$—Q, and a C$_{1-6}$ straight or branched alkyl chain substituted with one R$^d$ group, wherein A is as originally described;

R$^d$ is independently selected —R* or Q;

Q is selected from the group consisting of:

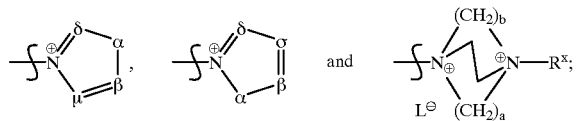

wherein

L$^-$, a and b are as originally defined, and R$^x$ represents a member selected from the group consisting of: hydrogen or a C$_{1-8}$ straight- or branched-chain alkyl, optionally interrupted by one or two of O, S, SO, SO$_2$, NR$^w$, N$^+$R$^h$R$^w$, or —C(O)—, said chain being unsubstituted or substituted with one to four of halo, CN, NO$_2$, OR$^w$, SR$^w$, SOR$^w$, SO$_2$R$^w$, NR$^h$R$^w$, N$^+$(R$^h$)$_2$R$^w$, —C(O)—R$^w$, C(O)NR$^h$R$^w$, SO$_2$NR$^h$R$^w$, CO$_2$R$^w$, OC(O)R$^w$, OC(O)NR$^h$R$^w$, NR$^h$C(O)R$^w$, NR$^h$C(O)NR$^h$R$^w$, phenyl or heteroaryl, said phenyl and heteroaryl group being optionally substituted with from one to four R$^i$ groups or with one to two C$_{1-3}$ straight or branched chain alkyl groups, said alkyl groups being unsubstituted or substituted with one to four R$^i$ groups;

R* is selected from:

wherein d represents NR$^k$; R$^k$ represents —C$_{1-6}$ straight or branched chain alkyl; and e, g, x and y represent CR$^m$ or N$^+$R$^k$, with R$^k$ as defined above and R$^m$ representing hydrogen.

A still more preferred subset of compounds of the invention is represented by formula Ia wherein:

R represents

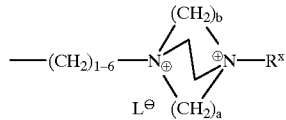

and R$^x$, a, b and L$^-$ are as originally defined.

Another more preferred subset of compounds of the invention is represented by formula Ib wherein:

R represents

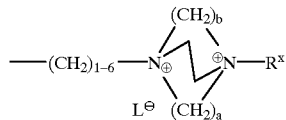

and R$^x$, a, b and L– are as originally defined.

Within the subsets, all other variables are as originally defined with respect to formula I.

Representative examples of compounds of the invention are shown below. The invention is intended, where appropriate, to include protonated amines protonated at the appropriate pH, e.g., pH 7.

E-1

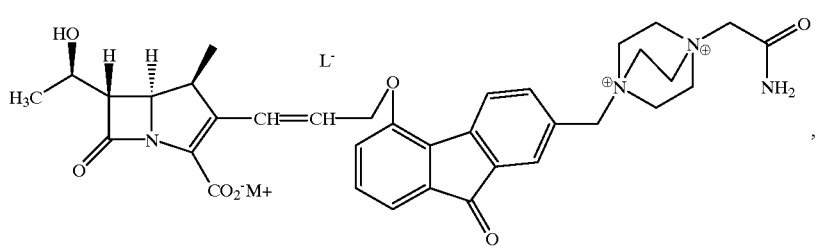

E-2

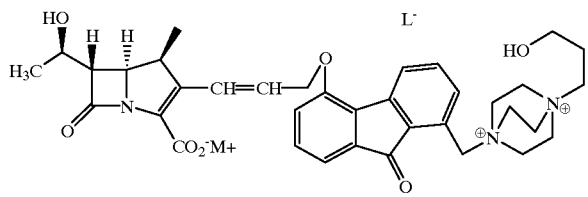

E-3

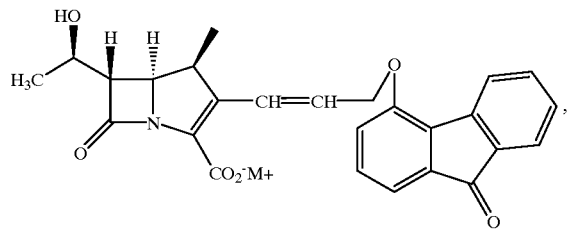

-continued
E-4
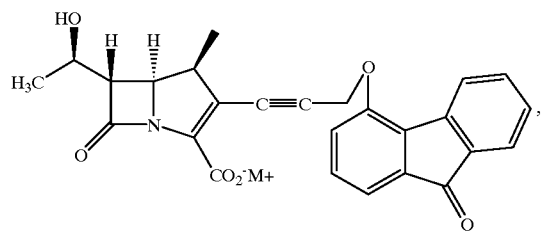
E-5
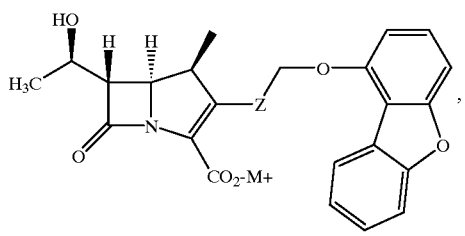
E-6
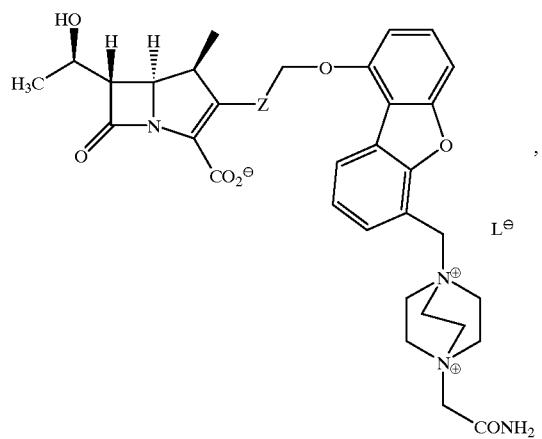
E-7
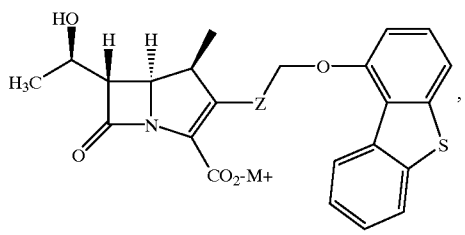
E-8
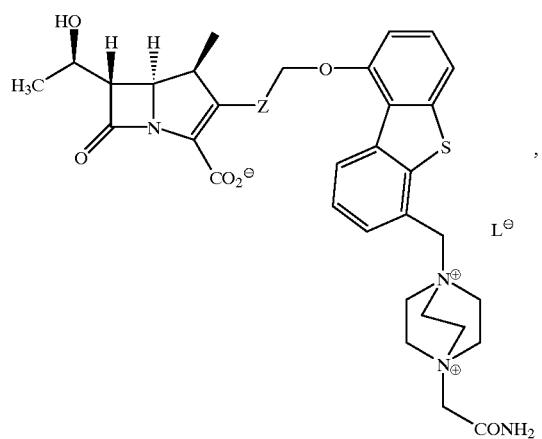
E-9
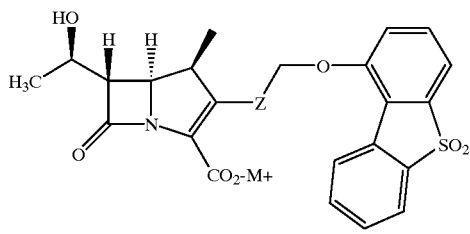
E-10
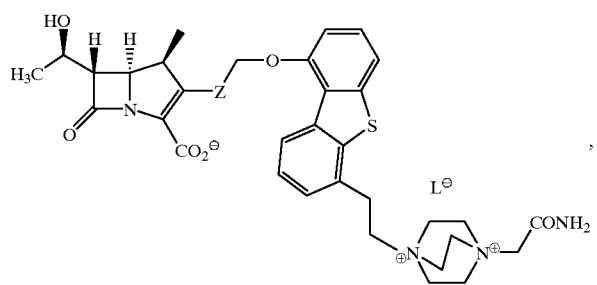
E-11
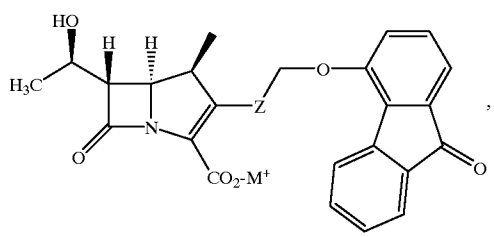

-continued
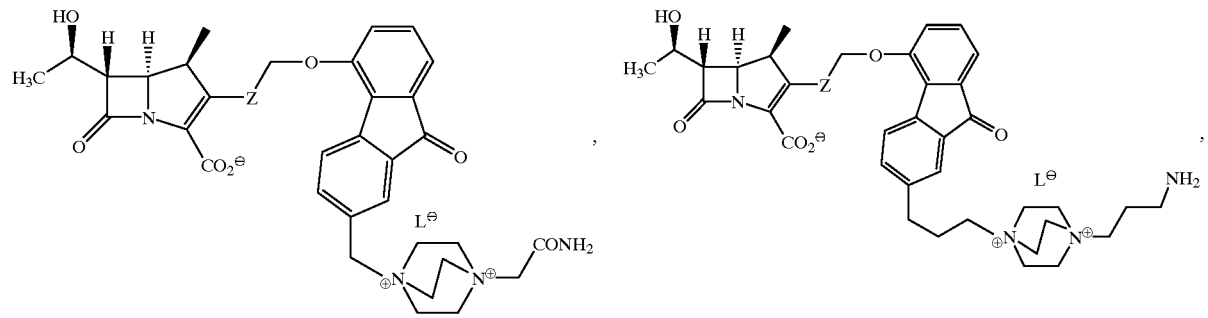
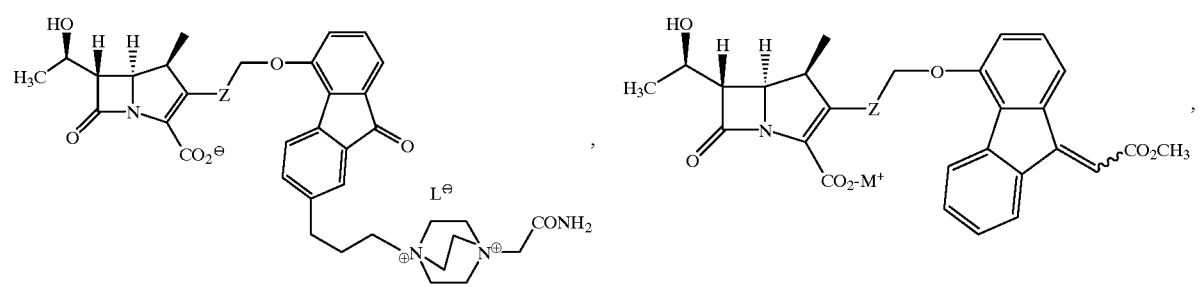
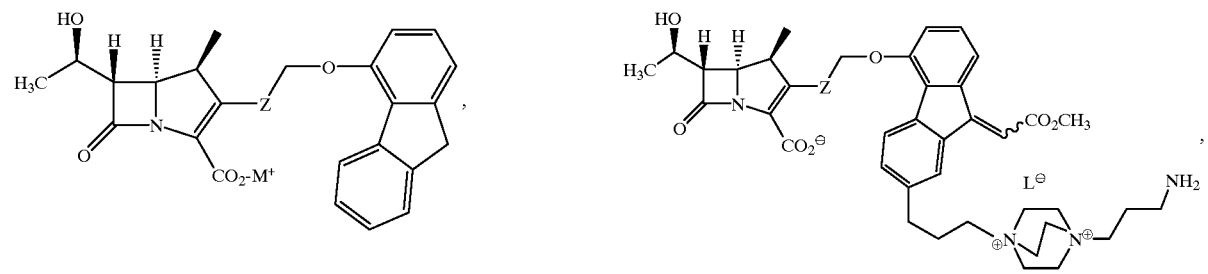
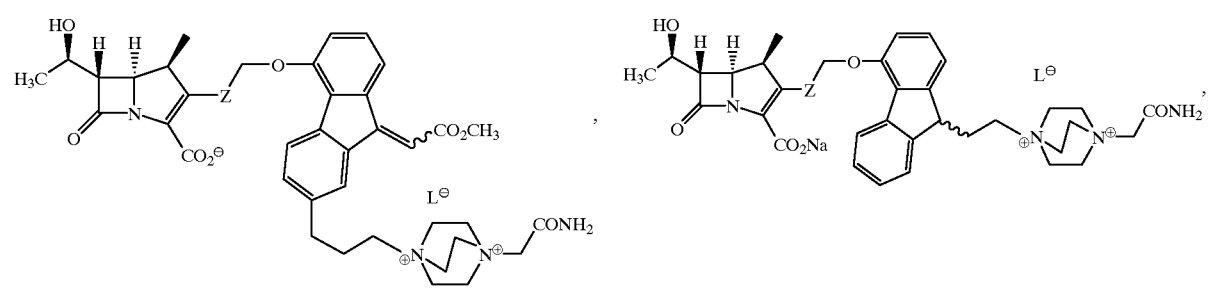
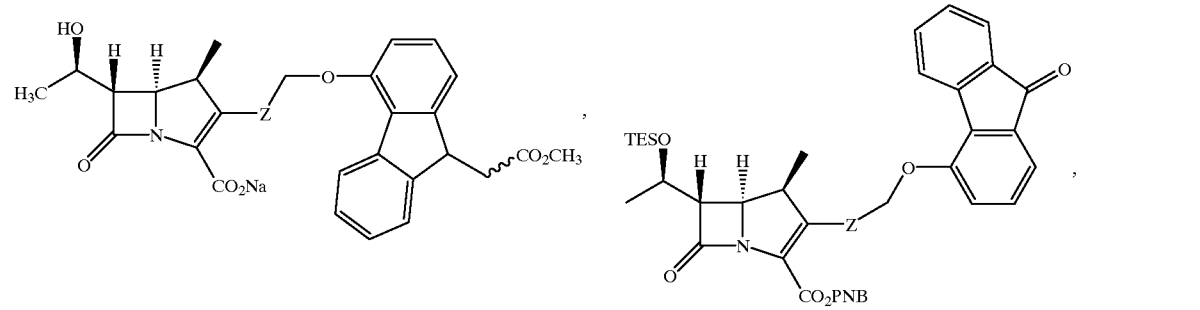

-continued
E-22
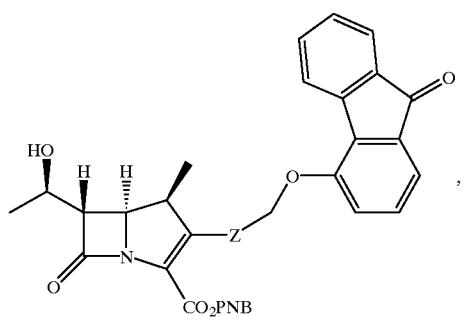
E-23
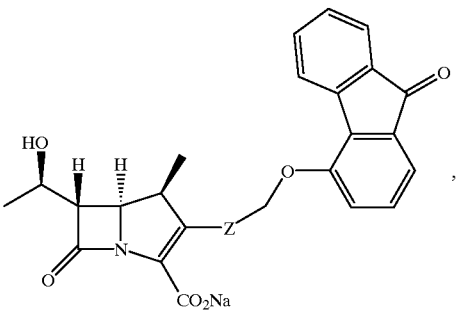
E-24
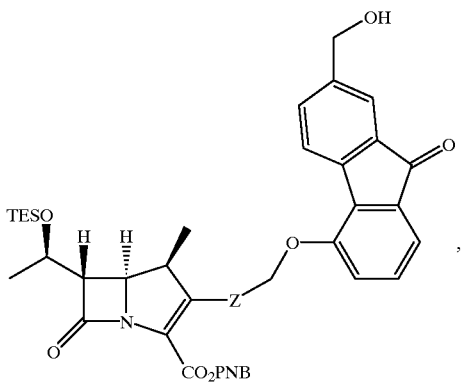
E-25
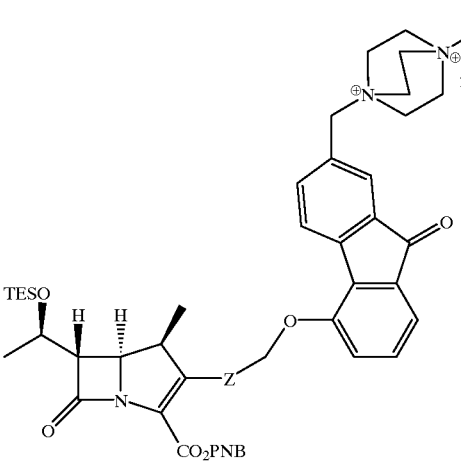
E-26
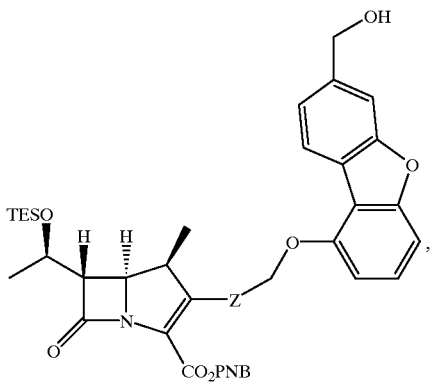
E-27
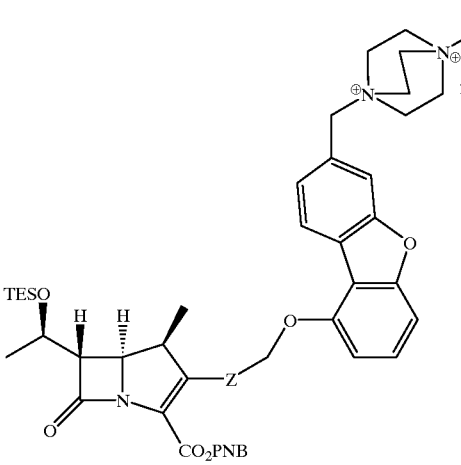

-continued

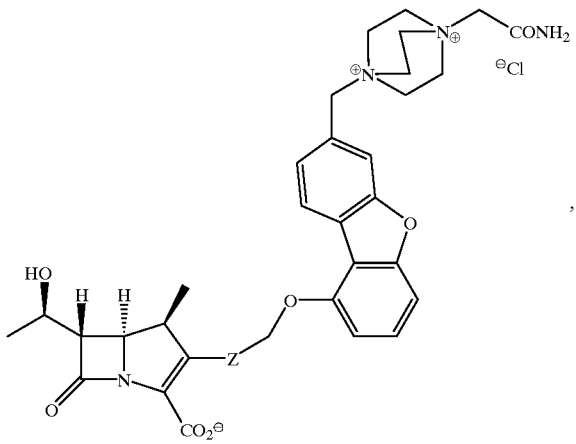

E-28 or a pharmaceutically acceptable salt thereof, wherein Z represents trans-ethenediyl, or ethynediyl group and $L^+$ represents a positively charged counterion, e.g. $Na^+$, $K^+$, or an appropriate molar amount of a divalent cation, e.g., $Ca^{+2}$.

The compounds of the present invention are prepared as depicted in Flow sheets A and B. The vinyl linked carbapenems are prepared, as shown in Flow sheet A, by reacting a suitably protected, activated 2-triflyl-carbapen-2-em-3-carboxylate A1 with a hydroxy allylic trialkyl stannane, to produce A2, and then reacting the condensed biaryl under Mitsunobu conditions to produce A3. Removing any protecting groups which are present affords the desired final vinyllic product A4.

FLOW SHEET A

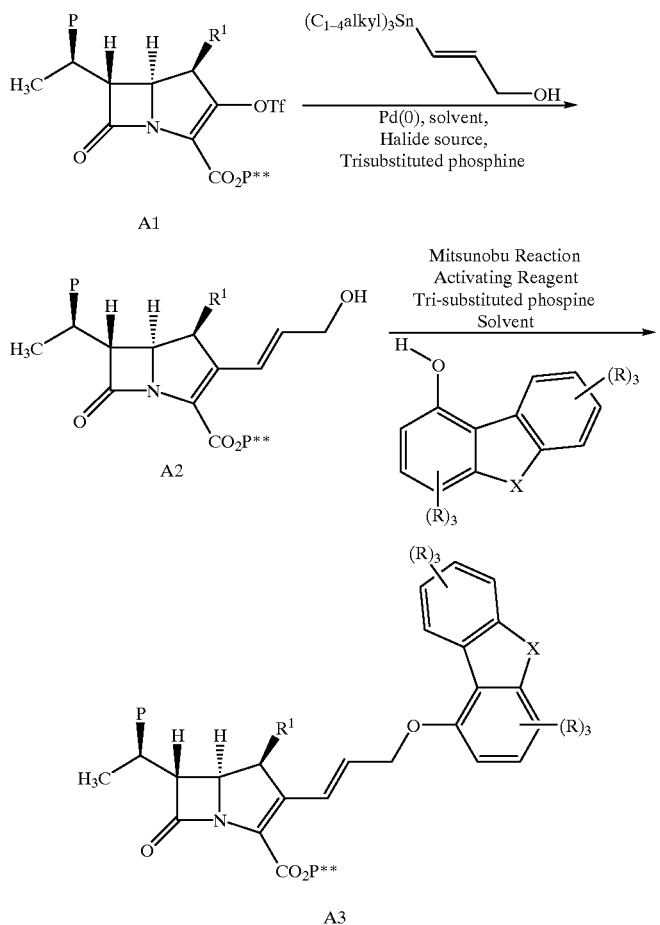

A3 →(Deprotect)

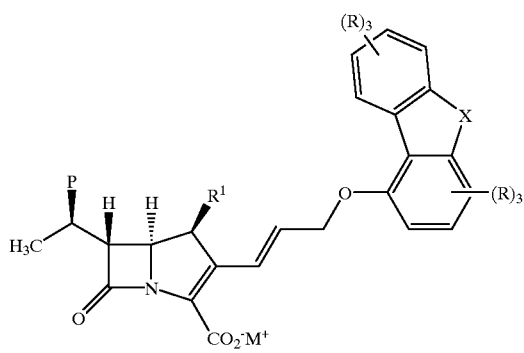

A4

The acetylenic linked carbapenems are prepared as shown in Flow sheet B in which intermediate A1 is reacted with a protected hydroxy propargylic trialkyl stannane to produce A5, deprotecting the propargylic hydroxy group to produce A6, and then reacting the condensed biaryl under Mitsunobu conditions to produce A7. Removing any protecting groups which are present affords the desired final acetylenic product A8.

FLOW SHEET B

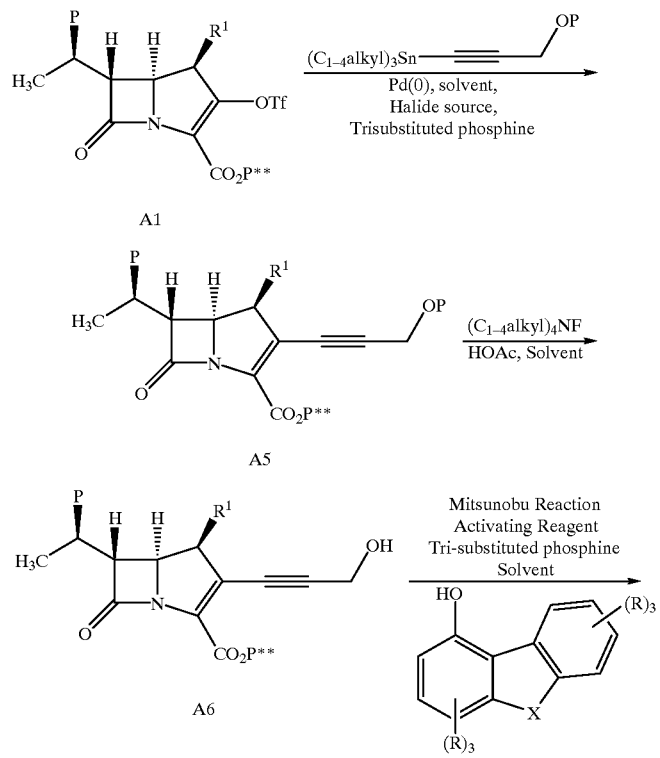

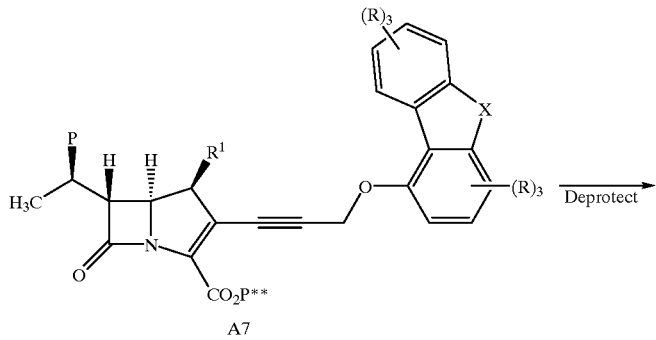

A7

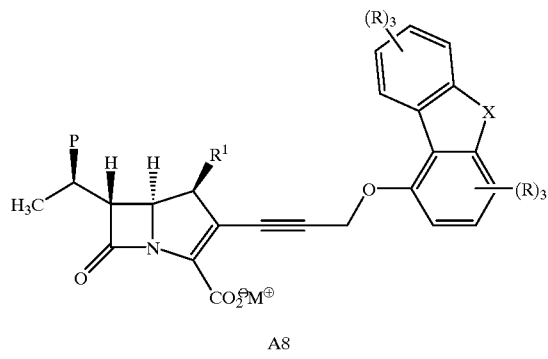

A8

Flow Sheet C describes the synthesis of the condensed biaryl carbapenem that possess a charged group Q, as previously defined. Typically, the intermediates A3 and A7 from Flow Sheets A and B possess an R group, as previously defined, which allows for the introduction of Q. Thus, generalized intermediate A9 is selectively deprotected to produce alcohol A10, which in term is activated for displacement with Q by conversion to intermediate A11. A11 is reacted with Q to form the quaternary ammonium intermediate A12. Removal of any protecting groups affords the final product A13.

FLOW SHEET C

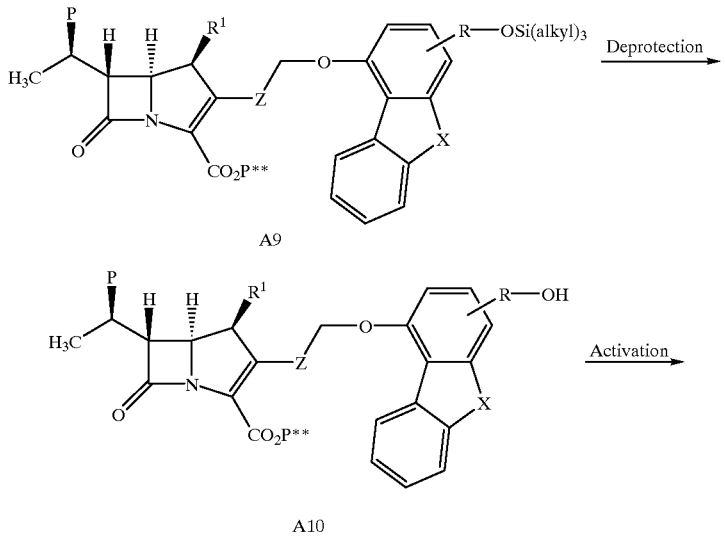

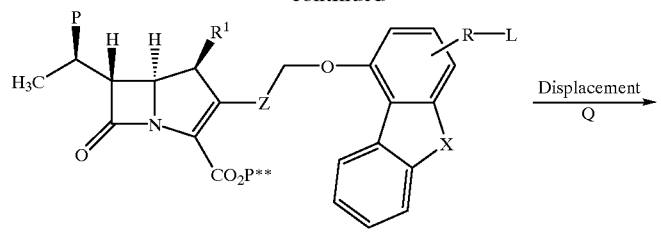

A11

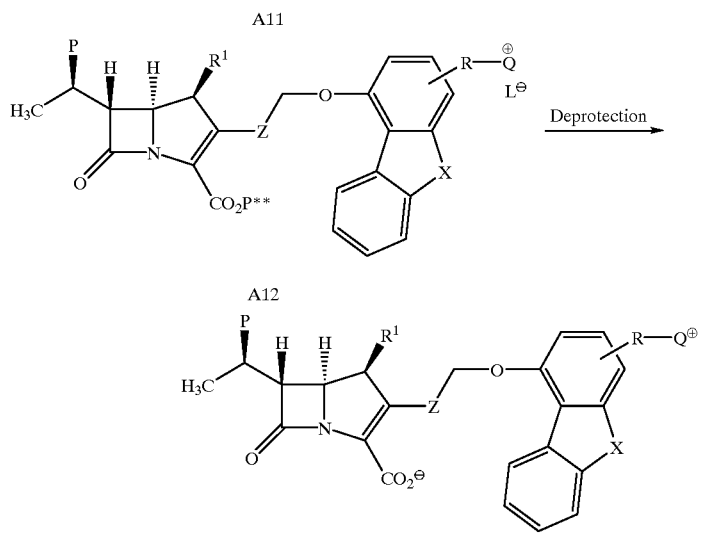

A12

A13

With reference to the flow sheets above, P, $R^1$, R, and M, are as defined with respect to the compounds of formula I, except that $M^+$ may be a metal cation, e.g., $Na^+$. See Dykstra et al., *Tet. Lett.*, 1998, 39, pg. 1865.

P** represents a carboxyl protecting group.

Many of compounds of the present invention are biologically active against MRSA/MRCNS. In vitro antibacterial activity is predictive of in vivo activity when the compounds are administered to a mammal infected with a susceptible bacterial organism.

Using standard susceptibility tests, the compounds of the invention are determined to be active against MRSA.

The compounds of the invention can be formulated in pharmaceutical compositions by combining the compound with a pharmaceutically acceptable carrier. Examples of such carriers are set forth below.

The compounds may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral composions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ dosage amounts in the range of from about 250 mg to 1000 mg. In parenteral administration, the unit dosage will typically include the pure compound in sterile water solution or in the form of a soluble powder intended for solution, which can be adjusted to neutral pH and isotonic.

The invention described herein also includes a method of treating a bacterial infection in a mammal in need of such treatment comprising administering to said mammal a compound of formula I in an amount effective to treat said infection.

The preferred methods of administration of the Formula I antibacterial compounds include oral and parenteral, e.g., i.v. infusion, i.v. bolus and i.m. injection.

For adults, about 5–50 mg of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

The compounds of Formula I are of the broad class known as carbapenems. Many carbapenems are susceptible to attack by a renal enzyme known as dehydropeptidase (DHP). This attack or degradation may reduce the efficacy of the carbapenem antibacterial agent. Many of the compounds of the present invention, on the other hand, are less subject to such attack, and therefore may not require the use of a DHP inhibitor. However, such use is optional and contemplated to be part of the present invention. Inhibitors of DHP and their use with carbapenems are disclosed in, e.g., [European Patent Application Nos. 79102616.4, filed Jul. 24, 1979 (Patent No. 0 007 614); and 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

The invention is further described in connection with the following non-limiting examples.

Preparative Example 1

Synthesis of 1-Hydroxydibenzothiophene

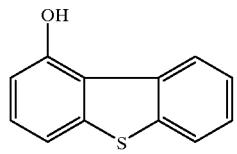

Step A

A stirred mixture of 3-methoxy benzenethiol (0.5 g, 3.6 mmoles), 1-flouro-2-nitrobenzene (0.5 g, 3.6 mmoles), 37% KF/Al$^2$O$_3$ (1.4755 g, 3 w/w), and 18-crown-6 (0.1255 g, 0.36 mmoles) in sieve-dried acetonitrile (5 mL) was refluxed at 90° C., under a N$_2$ atmosphere for 1 hr. The reaction was allowed to cool to ambient temperature. The insoluble solids present in the reaction were filtered off and washed with EtOAc. The filtrate was collected and concentrated in vacuo to give a black/red solid (1.1487 g). The product was purified by plate layer chromatography with a mixture of 2:1 hexane/CH$_2$Cl$_2$ to afford the desired product as a yellow solid (0.7095 g).

$^1$H NMR (CDCl$_3$) δ: 3.82 (s, 3H), 6.90 (dd, 1H), 7.01 (dd, 1H), 7.12–7.23 (m, 3H), 7.33–7.39 (m, 2H), 8.22 (dd, 1H).

Step B

To a stirred solution of the product obtained from Step A (0.7095 g, 2.7 mmoles) in absolute EtOH (7 mL) was added SnCl$_2$.H$_2$O (1.8563 g, 8.1 mmoles). The resulting mixture was refluxed at 90° C. for 1.5 hrs under an atmosphere of N$_2$. The reaction was cooled to ambient temperature, poured into a mixture of ice, brine, and 5 N NaOH, and extracted with EtOAc (2×). The organic layers were combined, washed with brine, and dried over Na$_2$SO$_4$. Concentration in vacuo afforded the desired product as a yellow oil (0.6826 g). The product was purified by plate layer chromatography with 1:1 CH$_2$Cl$_2$/hexane to give the desired amine.

$^1$H NMR (CDCl$_3$) δ: 3.72 (s, 3H), 4.29 (br s, 2 H), 6.62–6.69 (m, 3H), 6.73–6.80 (m, 2H), 7.11 (t, 1H), 7.21 (t, 1H), 7.44 (dd, 1H).

Step C

To a thick slurry of the amine (0.277 g, 1.74 mmoles) from Step B in 2 N HCl (1.76 mL) and HOAc (0.54 mL) was added absolute EtOH (1.76 mL) to solubilize the mixture. The stirred mixture was cooled to 0° C. and a solution of NaNO$_2$ (0.1552 g, 2.09 mmoles) in water (0.2 mL) was added under N$_2$. The resulting light brown solution was stirred at 0° C., for 20 min. before adding a 93.1 mg/mL aqueous solution of KPF$_6$ (2.7 mL). Upon addition, yellow solid immediately precipitated out of solution. The yellow/brown solid was collected by vacuum filtration and washed with cold water (2×) and cold Et$_2$O (3×). After drying in vacuo over 18 hrs, the diazonium salt was collected as a yellow solid (0.3149 g).

$^1$H NMR (d$_6$-acetone) δ: 3.83 (s, 3H), 7.16 (dd, 1H), 7.27 (s, 1H), 7.27–7.30 (dd, 1H), 7.47 (t, 1H), 7.79 (d, 1H), 7.88 (t, 1H), 8.18 (t, 1H), 8.84 (dd, 1H).

Step D

A solution of FeSO$_4$.7H$_2$O (0.2258 g, 0.81 mmoles) in distilled water (3 mL) was heated to 100° C. The diazonium salt from Step C was added in one portion and the resulting mixture was stirred at 100° C. under N$_2$. Gas evolution was observed for the first 5–10 min. of the reaction. With time, the product oiled out of solution. After 30 min., the reaction was partitioned between EtOAc and ice/brine. The organic layer was collected, dried over Na$_2$SO$_4$, and concentrated in vacuo to give a green/brown oil (0.3317 g). The crude material was purified by plate layer chromatography with 20% CH$_2$Cl$_2$/hexane to afford the desired product as a white solid (0.040 g).

$^1$H NMR (CDCl$_3$) δ: 4.07 (s, 3H), 6.89 (d, 1H), 7.36–7.45 (m, 4H), 7.80 (dd, 1H), 8.64 (dd, 1H).

Step E

To a stirred solution of the dibenzothiophene (0.040 g, 0.19 mmoles) isolated from Step D in HOAc (2.5 mL) was added 40% HBr (0.65 mL, 5.6 mmoles) under N$_2$. The reaction was heated to 130° C. for 20 hrs. The resulting green solution was partitioned between EtOAc and ice/brine. The organic layer was washed with sat. NaHCO$_3$ (2×) and brine. The EtOAc extract was dried over Na$_2$SO$_4$ and concentrated in vacuo to give an off-white solid (0.0366 g). Purification by plate layer chromatography with 1:1 hexane/CH$_2$Cl$_2$ afforded the desired phenol as a white solid (0.0294 g).

¹H NMR (CDCl₃) δ: 5.53 (s, 1H), 6.77 (d, 1H), 7.26 (t, 1H), 7.43–7.49 (m, 3H), 7.82 (dd, 1H), 8.63 (dd, 1H).

Preparative Example 2

Preparation of 1-Hydroxy-5-T-Butyldimethylsilyloxymethyl Dibenzothiophene

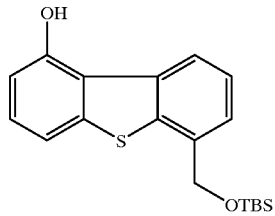

Step A

2-Bromo-3-nitrotoluene and 3-methoxy benzenethiol were coupled using the procedures described in Example 1 (Step A) to afford the desired product as a yellow oil.

¹H NMR (CDCl₃) δ: 2.38 (s, 3H), 3.73 (s, 3H), 6.62–6.66 (m, 2H), 6.68 (dd, 1H), 7.11 (t, 1H), 7.39 (m, 2H), 7.53 (dd, 1H).

Step B

The coupled product from Step A was reduced to its corresponding amine using the procedures described in Example 2 (Step B). The amine was obtained as a green/yellow oil.

¹H NMR (CDCl₃) δ: 2.39 (s, 3H), 3.71 (s, 3H), 6.58–6.65 (m, 3H), 6.71–6.76 (m, 2H), 7.09 (q, 2H).

Step C

Utilizing the procedure described in Example 2 (Step C), the amine from Step B was converted to its diazonium salt. The product was isolated as a green/yellow solid.

¹H NMR (d6-acetone) δ: 2.49 (s, 3H), 3.78 (s, 3H), 6.97–7.02 (m, 3H), 7.35 (t, 1H), 8.04 (t, 1H), 8.31 (d, 1H), 8.87 (d, 1H).

Step D

To a solution of the diazonium salt (0.9275 g, 2.3 mmoles) obtained from Step C in anhydrous DMSO (20 mL) was added 3A molecular sieves. The mixture was heated to 60° C. and stirred for 1 hr. The orange mixture was filtered and the molecular sieves washed well with EtOAc. The filtrate was collected and washed with H₂O (4×) followed by brine. The organic layer was dried over Na₂SO₄ and concentrated in vacuo to give a dark red/orange oil. The crude material was purified by plate layer chromatography with 2:1 hexane/CH₂Cl₂ to give the desired dibenzothiophene as a white solid (0.1047 g).

¹H NMR (CDCl₃) δ: 2.58 (s, 3H), 4.08 (s, 3H), 6.91 (d, 1H), 7.25 (d, 1H), 7.36 (t, 2H), 7.47 (d, 1H), 8.50 (d, 1H).

Step E

Utilizing the procedure described in Example 2 (Step E), the product from Step D was demethylated to give the phenol as a white solid.

1 H NMR (CDCl₃) δ: 2.58 (s, 3H), 6.77 (d, 1H), 7.24–7.31 (2d, 2H), 7.38 (t, 1H), 7.43 (t, 1H), 8.48 (d, 1H).

Step F

To a solution of the phenol (0.076 g, 0.35 mmoles) from Step E in CH₂Cl₂ (1 mL) was added NEt₃ (0.059 mL, 0.42 mmoles) at 0° C. under N₂. The reaction was stirred for 10 min. before adding acetyl chloride (0.027 mL, 0.39 mmoles). The reaction was then stirred at 0° C. for another 15 min. and poured into ice/H₂O. The mixture was extracted with EtOAc. The organic layers were washed with 1 N HCl followed by brine, and dried over Na₂SO₄. Concentration in vacuo gave the desired product as a light brown oil (0.1163 g).

¹H NMR (CDCl₃) δ: 2.53 (s, 3H), 2.57 (s, 3H), 7.19 (d, 1H), 7.27 (d, 1H), 7.38 (t, 1H), 7.43 (t, 1H), 7.73 (d, 1H), 8.08 (d, 1H).

Step G

The acetylated product (0.0902, 0.35 mmoles) obtained from Step F was dissolved in CCl₄ (0.5 mL) and placed under a N₂ atmosphere. NBS (0.0817 g, 0.46 mmoles) was added followed by a crystal of AIBN. The reaction was heated to 80° C. for 23 hrs. The reaction was poured into ice/brine and extracted with EtOAc. The organic layers were washed with 5% Na₂S₂O₃ and brine. Concentration in vacuo gave the crude product as a yellow oil (0.2085 g). The oil was purified by plate layer chromatography with 1:1 hexane/CH₂Cl₂ to afford the alkyl bromide as a yellow solid (0.0895 g).

¹H NMR (CDCl₃) δ: 2.53 (s, 3H), 4.77 (s, 2H), 7.23 (d, 1H), 7.46–7.52 (m, 3H), 7.76 (d, 1H), 8.22 (dd, 1H).

Step H

The alkyl bromide (0.0895 g, 0.27 mmoles) from Step G was combined with KOAc (0.0541 g, 0.53 mmoles) in sieve-dried DMF (1 mL) and heated to 100° C. for 1 hr. The reaction was poured into ice/H₂O and extracted with EtOAc. The organic layers were washed with additional H₂O (2×) and brine, and dried over Na₂SO₄. Concentration in vacuo gave an orange/red oil (0.114 g). The oil was purified by plate layer chromatography with 3:1 CH₂Cl₂/hexane to give a pale yellow solid (0.0635 g).

¹H NMR (CDCl₃) δ: 2.17 (s, 3H), 2.55 (s, 3H), 5.38 (s, 2H), 7.21 (d, 1H), 7.44–7.49 (m, 3H), 7.73 (d, 1H), 8.22 (dd, 1H).

Step I

A yellow mixture of the product (0.0635 g, 0.2 mmoles) from Step H, 5 N NaOH (0.1 mL, 0.42 mmoles), and absolute EtOH (1 mL) was heated to 70° C. under N₂ for 15 min. The reaction was partitioned between EtOAc and ice/1 N HCl. The organic layer was washed with brine, dried over Na₂SO₄, and concentrated in vacuo to give an orange solid (0.0637 g). The solid was purified by plate layer chromatography with 5% EtOAc/CH₂Cl₂ to give the desired product as a slightly orange solid (0.0335g).

¹H NMR (CDCl₃+CD₃OD) δ: 4.76 (s, 2H), 6.71 (d, 1H), 7.07 (t, 1H), 7.17 (d, 1H), 7.24–7.28 (m, 2H), 8.45 (d, 1H).

Step J

To a flask charged with the phenol (0.0335 g, 0.16 mmoles) from Step I was added a solution of TBSCl (0.0305 g, 0.17 mmoles) in DMF (0.5 mL) under N2. The reaction was cooled to 0° C. and stirred for 10 min. before adding dropwise a solution of imidazole (0.0137 g, 0.19 mmoles) in DMF (0.25 mL). The solution was stirred at 0° C. for 1 h. The reaction was partitioned between EtOAc and ice/1 N HCl. The organic layer was washed with brine, dried over Na₂SO₄, and concentrated in vacuo to give a light brown oil. The oil was purified by plate layer chromatography with 3:1 CH₂Cl₂/hexane to afford the TBS-protected alcohol as a light yellow solid (0.0416 g).

¹H NMR (CDCl₃) δ: 0.15 (s, 3H), 0.98 (s, 6H), 4.97 (s, 2H), 6.76 (d, 1H), 7.26 (t, 1H), 7.45–7.48 (m, 3H), 8.55 (dd, 1H).

Preparative Example 3

Preparation of 1-Hydroxy-5-T-Butyldimethylsilyloxypropyl Dibenzothiophene

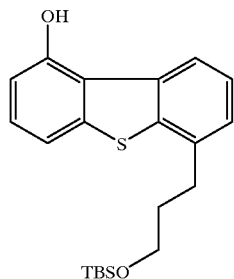

Step A

The acetylated dibenzothiophene (0.3985, 1.55 mmoles) obtained from Example 2 (Step F) was dissolved in $CCl_4$ (5 mL) and place under a $N_2$ atmosphere. Recrystallized NBS (0.3051 g, 1.7 mmoles) was added followed by a crystal of AIBN. The reaction was heated to 80° C. for 23 hrs. Additional NBS (0.3067 g, 1.7 mmoles) was added to the reaction and the mixture was stirred at 80° C. for another 6.5 hrs. The reaction was poured into ice/brine and extracted with EtOAc. The organic layers were washed with 5% $Na_2S_2O_3$ and brine. Concentration in vacuo gave an orange solid (0.5974 g). By $^1H$ NMR analysis, the crude product contained a 3:1 mixture of the desired dibrominated product to the monobrominated product or the dibrominated product.

$^1H$ NMR ($CDCl_3$) δ: 2.55 (s, 3H), 6.96 (s, 1H), 7.25 (d, 1H), 7.48–7.50 (m, 2H), 7.76 (t, 2H), 8.24 (d, 1H).

Step B

The crude alkyl bromide (0.4670 g, 1.1 mmoles) from Step A was dissolved in sieve-dried DMF (5 mL) and placed under $N_2$. KOAc (0.3396 g, 3.4 mmoles) was added in one portion and the reaction was heated to 100° C. After 1.5 hrs, The reaction was partitioned between EtOAc and $H_2O$. The organic layer was washed with water (3x) and brine, dried over $Na_2SO_4$, and concentrated in vacuo to give a brown-lyellow oil (0.6382 g). The oil was purified by plate layer chromatography with 4 elutions using 3:2 $CH_2Cl_2$/hexane to give 2 major fractions: 1) the triacetate compound (0.1403 g) and 2) a mixture of the diacetate compound and the aldehyde (0.2077 g).

$^1H$ NMR ($CDCl_3$) δ: 2.18 (s, 6H), 2.55 (s, 3H), 7.23 (d, 1H), 7.47 (t, 2H), 7.61 (d, 1H), 7.75 (d, 1H), 7.93 (s, 1H), 8.31 (dd, 1H).

Step C

The fraction from Step B containing the triacetate compound (0.1255 g, 0.4 mmoles) was suspended in absolute EtOH (2 mL) and 5 N NaOH (0.15 mL, 0.8 mmoles) was added under $N_2$. The reaction was heated to 70° C. for 20 min. then poured into ice/1 M HCl. The mixture was extracted with EtOAc. The organic layer was collected, washed with brine, dried over $Na_2SO_4$, and cocentrated in vacuo to give an orange solid (0.1065 g). The solid was purified by plate layer chromatography with 5% EtOAc/$CH_2Cl_2$ to afford the clean aldehyde as a yellow solid (0.0756 g).

$^1H$ NMR ($CDCl_3+d_6$-acetone) δ: 6.73 (d, 1H), 7.07 (t, 1H), 7.21 (d, 1H), 7.40 (t, 1H), 7.73 (d, 1H), 8.78 (dd, 1H), 9.00 (bs, 1 H), 10.04 (s, 1H).

Step D

The fraction from Step B containing a mixture of the diacetate compound and the aldehyde (0.2077 g, 0.77 moles) was submitted under the same reaction conditions described in Step C. The resulting mixture of aldehyde and diol was separated by plate layer chromatography with 5% EtOA/$CH_2Cl_2$ to give 0.0895 g of clean aldehyde.

Step E

The aldehydes from Step C and Step D were combined and acetylated using the procedures described in Example 3 (Step F). The reaction was stirred at 0° C. for a total of 30 min. The desired product was isolated as tan solid.

$^1H$ NMR ($CDCl_3$) δ: 2.57 (s, 3 H), 7.29 (d, 1H), 7.50 (t, 1H), 7.65 (t 1H), 7.82 (d, 1H), 7.99 (dd, 1H), 8.54 (dd, 1H), 10.29 (s, 1H).

Step F

The acetylated product (0.1572 g, 0.58 mmoles) from Step E was dissolved in $CH_2Cl_2$ (3 mL) and methyl (triphenylphosphoranylidene)-acetate (0.2141 g, 0.64 mmoles) was added under $N_2$. The mixture was stirred at ambient temperature for 1.5 hrs. The reaction was concentrated in vacuo to give a white/yellow solid. The solid was purified by plate layer chromatography with 5% hexane/$CH_2Cl_2$ to give the desired ester as a white solid (0.1688 g).

$^1H$ NMR ($CDCl_3$) δ: 2.54 (s, 3 H), 3.86 (s, 3H), 6.67 (d, 1H), 7.24 (d, 1H), 7.48 (t 2H), 7.66 (d, 1H), 7.77 (d, 1H), 7.95 (d, 1H), 8.28 (d, 1H).

Step G

To a solution of the ester obtained from Step F (0.1688 g, 0.51 mmoles) in 1:1 EtOAc/EtOH was added 10% Pd/C (0.0186, 10% w/w). The resulting mixture was degassed with $N_2$ and hydrogenated under atmospheric $H_2$ pressure for 3 hrs. The reaction was degassed with $N_2$ and the catalyst removed by filtering through a celite pad. The filtrate was concentrated in vacuo to give a white/yellow solid (0.1595 g).

$^1H$ NMR ($CDCl_3$) δ: 2.53 (s, 3 H), 2.80 (t, 2H), 3.21 (t, 2H), 3.70 (s, 3H), 7.21 (t, 1H), 7.31 (d, 1H), 7.40–7.49 (m, 2H), 7.73 (dd, 1H), 8.12 (dd, 1H).

Step H

The alkyl ester isolated from Step G (0.1595 g, 0.49 mmoles) was dissolved in absolute EtOH (2 mL) and 5 N NaOH (0.29 mL, 1.5 mmoles) was added under $N_2$. The resulting yellow mixture was heated to 70° C. After 1 hr, the reaction was partitioned between ice/1 M HCl and EtOAc. The organic layer was washed with brine, dried over $Na_2SO_4$, and concentrated in vacuo to afford the desired acid as a pale yellow solid (0.1614 g).

$^1H$ NMR ($CDCl_3+d_6$-acetone) δ: 2.77 (t, 2H), 3.15 (t, 2H), 6.81 (d, 1H), 7.18–7.26 (m, 2H), 7.32 (t, 1H), 7.32 (d, 1H), 8.52 (d, 1H).

Step I

To a solution of the carboxylic acid generated in Step H (0.1614, 0.49 mmoles) in distilled THF (5 mL) was added dropwise a 1 M solution of BH3.THF in THF (0.98 mL, 0.98 mmoles). Upon addition, gas evolution was observed. With time, the reaction became a cloudy green mixture. The reaction was stirred at ambient temperature for a total of 2 hrs. The reaction was quenched with dropwise addition of MeOH until no further gas evolution was observed. The reaction mixture was concentrated in vacuo and the residue was purified by plate layer chromatography with 5% EtOAc/$CH_2Cl_2$ to give the desired diol as a white solid (0.1065 g).

$^1H$ NMR ($CDCl_3+d_6$-acetone) δ: 1.88 (m, 2H), 2.81 (t, 2H), 3.57 (t, 2H), 6.74 (d, 1H), 7.08 (t, 2H), 7.10 (d, 1H), 7.21–7.27 (m, 2H), 8.42 (d, 1H), 8.69 (bs, 1 H).

Step J

Utilizing the procedure described in Example 3 (Step J), the diol obtained from Step I was selectively protected at the primary alcohol position to give the desired TBS-protected product as a yellow oil after plate layer chromatography with 5% EtOAc/CH$_2$Cl$_2$.

$^1$H NMR (CDCl$_3$) δ: 0.07 (s, 3H), 0.92 (s, 6 H), 1.99 (m, 2H), 2.92 (t, 2H), 3.70 (t, 2H), 6.74 (d, 1H), 7.24–7.27 (m, 2H), 7.38–7.43 (m, 2H), 8.48 (d, 1H).

Preparative Example 4

Preparation of 1-Hydroxy-5-T-Butyldimethylsilyloxymethyl Dibenzofuran

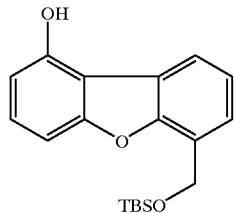

Step A

To a mixture of 2,6-difluoronitrobenzene (1.0 g, 6.3 mmoles) in MeOH (10 mL) was added a 4.4 M solution of NaOMe in MeOH (1.57 mL, 6.9 mmoles). The mixture was heated to 70° C. for 20 min. The resulting orange reaction mixture was concentrated in vacuo. The residue was dissolved in EtOAc and washed with HO and brine. The organic layer was dried over Na$_2$SO$_4$ and concentrated in vacuo to give a pale yellow solid. The solid was purified by plate layer chromatography with 1:1 hexane/CH$_2$Cl$_2$ to give clean product as a pale yellow solid (1.0559 g).

$^1$H NMR (CDCl$_3$) δ: 3.89 (s, 3H), 6.77–6.85 (m, 2H), 7.36–7.41 (m, 1H).

Step B

The methoxy nitrobenzene isolated from Step A was coupled with o-cresol (0.64 mL, 6.2 mmoles) using the procedures described in Example 3 (Step A) with the exception that the reaction time was 3 hrs. After purification by plate layer chromatography with 1:1 hexane/CH$_2$Cl$_2$, the desired adduct was obtained as a pale yellow solid.

$^1$H NMR (CDCl$_3$) δ: 2.18 (s, 3H), 3.91 (s, 3H), 6.27 (d, 1H), 6.66 (d, 1H), 6.98 (d, 1H), 7.10–7.27 (m, 4H).

Step C

The adduct from Step B (1.3924 g, 5.4 mmoles) was hydrogenated under 40–46 psi of H$_2$ in a Parr Shaker for 5 days using 10% Pd/C (0.139 g, 10 w/w) in 1:1 EtOH/EtOAc. The catalyst was filtered off through a celite pad and the filtrate was concentrated in vacuo. The product was obtained as a yellow oil (1.2833 g).

$^1$H NMR (CDCl$_3$) δ: 2.30 (s, 3H), 3.88 (s, 3H), 6.36 (m, 1H), 6.60 (m, 2H), 6.79 (d, 1H), 6.97 (t, 1H), 7.08 (t, 1H), 7.21 (d, 1H).

Step D

The amine from Step C was converted to its KPF$_6$ diazonium salt using the procedures described in Example 2 (Step C). The product was isolated as a yellow solid.

$^1$H NMR (d6-acetone) δ: 2.26 (s, 3H), 4.36 (s, 3H), 6.57 (d, 1H), 7.25 (d, 1H), 7.32 (d, 1H), 7.38 (t, 2H), 7.46 (dd, 1H), 8.17 (t, 1H).

Step E

A mixture of 0.438 g (0.48 mmoles) of Pd$_2$(dba)$_3$ in anhydrous DMSO (30 mL) was heated to 100° C. under N$_2$ and the diazonium salt from Step D (1.8489 g, 4.8 mmoles) was added in one portion, resulting in significant gas evolution. The reaction was stirred at 100° C. for 40 min and then filtered through celite. The filtrate was paritioned between EtOAc and water. The organic layer was washed well with H$_2$O (2x) followed by brine. The organic layer was dried over Na$_2$SO$_4$ and concentrated in vacuo to give a black solid. The solid was purified by plate layer chromatography with 2:1 hexane/CH$_2$Cl$_2$ to give the desired product as a white solid (0.4335 g).

$^1$H NMR (CDCl$_3$) δ: 2.59 (s, 3H), 4.05 (s, 3H), 6.77 (d, 1H), 7.20–7.27 (m, 3H), 7.35 (t, 1H), 7.95 (dd, 1H).

Step F

The dibenzofuran from Step E was demethylated and acetylated using the procedures described in Example 2 (Step E) and Example 3 (Step F) respectively. The desired product was obtained as a white solid over the 2 steps.

$^1$H NMR (CDCl$_3$) δ: 2.50 (s, 3H), 2.58 (s, 3H), 7.11 (dd, 1H), 7.21–7.30 (m, 2H), 7.41–7.50 (m, 2H), 7.64 (dd, 1H).

Step G 0.1126 g (0.49 mmoles) of acetylated dibenzofuran from Step F, recrystallized NBS (0.0970 g, 0.54 mmoles), benzoyl peroxide (0.0271 g, 0.099 mmoles), and CCl$_4$ (3 mL) were combined under N$_2$ and heated to 100° C. In addition to heating, the reaction was illuminated with a sun lamp. Within 30 min., the reaction became dark purple. After 2 hrs, another 0.3 equivalents of NBS and 0.0312 g of benzoyl peroxide were added. The reaction was heated for another 2 hrs, and then partitioned between EtOAc and 5% Na$_2$S$_2$O$_3$. The organic layer was washed with H$_2$O and brine, dried over Na$_2$SO$_4$, and concentrated in vacuo to give a dark purple solid. The solid was purified by plate layer chromatography with 2:1 CH$_2$Cl$_2$/hexane to afford the desired alkyl bromide as an off-white solid (0.081 g).

$^1$H NMR (CDCl$_3$) δ: 2.50 (s, 3H), 4.84 (s, 2H), 7.16 (dd, 1H), 7.30 (t, 1H), 7.47–7.55 (m, 3H), 7.77 (dd, 1H).

Step H

The diacetate was prepared after plate layer chromatography with 2:1 CH2Cl2/hexane, from the alkyl bromide of Step G using the procedures described in Example 3 (Step H).

$^1$H NMR (CDCl$_3$) δ: 2.14 (s, 3H), 2.51 (s, 3H), 5.49 (s, 2H), 7.15 (dd, 1H), 7.32 (t, 1H), 7.44–7.52 (m, 3H), 7.80 (dd, 1H).

Step I

The diacetate from Step H was treated under the same conditions as Example 3 (Step I) to give the crude diol.

$^1$H NMR (CDCl$_3$+CD$_3$OD) δ: 5.00 (s, 2H), 6.67 (d, 1H), 7.03 (d, 1H), 7.19–7.30 (m, 2H), 7.38 (dd, 1H), 8.02 (dd, 1H).

Step J

The diol from Step I was selectively protected at the primary position using the procedures described in Example 3 (Step J) to give the desired product as a white solid after plate layer chromatography with 2:1 CH$_2$Cl$_2$/hexane.

$^1$H NMR (CDCl$_3$) δ: 0.15 (s, 3H), 0.97 (s, 6H), 5.15 (s, 2H), 6.68 (d, 1H), 7.15 (d, 1H), 7.25 (t, 1H), 7.33 (t, 1H), 7.53 (d, 1H), 7.98 (d, 1H).

Preparative Example 5

Prepartion of 3-Hydroxybiphenyl

A stirred mixture of 660 mg(3 mmol) of 3-iodophenol, 439 mg (3.6 mmol) phenylboronic acid, and 173 mg (0.15 mmol) tetrakistriphenylphosphine in 10 mL of toluene, 5 mL ethanol, and 6 mL 2M sodium carbonate (aqueous) was heated at 100° C. in an inert atmosphere of nitrogen for 15 minutes. The cooled mixture was partitioned between EtOAc, ice, and brine and the organic phase was separated, washed with brine, dried over anhydrous Na$_2$SO$_4$, filtered and evaporated. The residue was purified by plate layer chromatography (PLC) using CH$_2$Cl$_2$ as the eluant to give 430 mg of the titled product.

¹H NMR (CDCl₃) δ: 1.26 (d, J=7.3 Hz,3H), 1.47 (d, J=6.3 Hz, 3H), 3.47 (dd, J=3.0, 11 Hz, 1H-6), 3.50 (m, 1H-1), and 4.2 (dd, J=3.0, 10 Hz, 1H-5).

Preparative Example 6

Preparation of 4'-T-Butyldiphenylsilyloxymethyl-3-Hydroxybiphenyl

As described in Preparative Example 5, 391 mg (1 mmol) of 4-t-butyldiphenylsilyloxymethylboronic acid (prepared as exemplified in U.S. Pat. No. 5,192,758) and 220 mg (1 mmol) of 3-iodophenol gave 354.3 mg of the title compound.

Preparative Example 7

Preparation of 4-Hydroxy-Fluorene

A partial solution of 196.2 mg (1 mmol) of 4-hydroxy-fluoren-9-one in 2 mL EtOAc and 3 mL EtOH with 40 mg 10% Pd/C was stirred under a balloon of hydrogen for 27.5 hours. The catalyst was removed by filtration through celite, washed well with EtOAc, and the filtrate evaporated. The residue was purified by plate layer chromatography with CH₂Cl₂-EtOAc(50:1) to give 102.7 mg of the title substance.

¹H NMR (d₆-acetone) δ: 3.88 (s, CH₂).

Preparative Example 8

Preparation of 4-Hydroxy-9-Carbomethoxy-Fluorylidene

A stirred mixture of 401 mg (2 mmol) of 4-hydroxy-fluoren-9-one and 1.37 g (4.1 mmol) of methyl-(triphenylphosphoranylidene)-acetate in 10 mL of toluene was refluxed under an atmosphere of nitrogen for 65.5 hours. The cooled reaction mixture was evaporated and the residue purified by plate layer chromatography using CH₂Cl₂-EtOAc (50:1) as eluant to give 433 mg of the title compound as a mixture of isomers.

¹H NMR (CDCl₃) δ: 3.87 (s, 3H), 3.88 (s, 3H), 6.74–8.89 (m, 8H).

Preparative Example 9

Preparation of 4-Hydroxy-9-Carbomethoxymethyl-Fluorene

A stirred mixture of 348 mg (1.38 mmol) of the fluorylidene derivative prepared in Preparative Example 8, and 50 mg of 10% Pd/C in 10 mL of EtOAc-EtOH (1:1) was hydrogenated under balloon pressure at ambient temperature for 2.5 hours. The catalyst was removed by filtration through celite, washed well with EtOAc, and the filtrate evaporated and dried in vacuo to give 348.5 mg of the title product.

¹H NMR (CDCl₃) δ: 2.77 (d, J=7.3 Hz, 2H), 3.79 (s, 3H), 4.42 (t, J=7.3 Hz,1H), 5.6 (s, OH), 6.72–8.09 (m, 7ArH).

Preparative Example 10

Preparation of 4-Hydroxy-9-Silyoxyethyl-Fluorene

Step A

Preparation of 4-Hydroxy-9-hydroxyethyl-fluorene

To a stirred solution of 277.5 mg (1.09 mmol) of the ester prepared in Preparative Example 9 in 5 mL of anhydrous THF at 0° C. was added dropwise 1.1 mL (1.1 mmol) of a 1M solution of lithium aluminum hydride in ether. The resulting mixture was stirred at 0° C. under nitrogen for 1.5 hours and then carefully quenched with Glaubers salt. The mixture was partitioned between EtOAc, ice, 2N HCl, and brine and the organic phase was separated, washed with brine, dried over Na₂SO₄, filtered, and evaporated. The residue was purified by PLC with CH₂Cl₂-EtOAc (10:1) to give 236.8 mg of the title compound.

¹H NMR (CDCl₃) δ: 2.33 (q, J=6.8 Hz, 2H), 3.57 (t, J=6.8 Hz, 2H), 4.13 (t, J=6.8 Hz), 6.08 (s, OH), 6.68–8.13 (m, 7ArH).

Step B

A mixture of 236.8 mg (1.05 mmol) of carbinol, prepared in the previous step, 173.5 mg (1.15 mmol) of t-butyldimethylchlorosilane, and 85.5 mg (1.26 mmol) of imidazole in 5 mL of sieve-dried DMF was stirred at 0° C. under nitrogen for 40 minutes. The mixture was partitioned between EtOAc, ice, 2N HCl, and the organic phase was separated, washed twice with ice-water and then with brine, dried over Na₂SO₄, filtered, and evaporated. The residue was purified by PLC with CH₂Cl₂-EtOAc (50:1) to give 325.1 mg of the title compound.

¹H NMR (CDCl₃) δ: 0.03 (s, 6H), 0.88 (s, 9H), 2.19(m, 2H), 3.67 (t, J=6.8 Hz, 2H), 4.13 (t, J=6.4 Hz), 5.12 (s, OH), 6.71–8.10 (m, 7ArH).

Preparative Example 11

Prepartion of 4-hydroxy-9-E,Z-t-butyldimethylsilyloxyethenyl-fluorene

Step A

Preparation of 4-Acetoxy-9-(2-t-butyldimethylsilyloxyethyl)-fluorene

To a stirred solution of a mixture of 1.91 g (5.6 mmol) of the phenol, prepared in Step B of Preparative Example 10, and 736.6 mg (7.28 mmol) of triethylamine in 20 mL of CH₂Cl₂ at 0° C. was added 527.5 mg (6.72 mmol) of neat acetyl chloride and the mixture was stirred further for 0.5 hour. The mixture was partitioned between EtOAc, ice, 1N HCl, and brine and the organic phase was separated, washed with brine, dried over Na₂SO₄, filtered, evaporated, and dried in vacuo to give 2.14 g of crude product which was used without further purification.

¹H NMR (CDCl₃) δ: 0.86 (s, 9H), 2.47 (s, 3H).

Step B

Preparation of 4-Acetoxy-9-bromo-9-(2-t-butyldimethylsilyloxyethyl)-fluorene

A mixture of 2.14 g (5.6 mmol) of material prepared in the previous step, 1.2 g (6.72 mmol) of N-bromosuccinimide, and a pinch of AIBN in 20 mL of carbon tetrachloride was refluxed under nitrogen for 1.5 hours. The cooled mixture was partitioned between EtOAc, ice, 5% aqueous sodium thiosulfate, and brine and the organic phase was separated, washed with brine, dried over Na₂SO₄, filtered, evaporated, and dried in vacuo to give the crude, title product which was used without further purification.

1H NMR (CDCl₃) δ: 0.73 (s, 9H), 2.47 (s, 3H), 2.91 (m, 2H), 3.20 (m, 2H).

Step C

Preparation of 4-Acetoxy-9-E,Z-t-butyldimethylsilyloxyethenyl-fluorene

A mixture of the crude product from the previous step, 913 mg (10.9 mmol) of NaHCO₃, and 1.54 g (5.98 mmol)

of silver triflate in 25 mL DMSO was stirred at room temperature for 15 minutes. The mixture was diluted with EtOAc, filtered through celite to remove the insoluble materials, and washed thoroughly with EtOAc. The filtrate was partitioned between EtOAc, ice, and brine and the organic phase was separated, washed twice with ice-water, and then with brine, dried over $Na_2SO_4$, filtered, evaporated, and dried in vacuo. Purification by PLC eluted with $CH_2Cl_2$-hexanes (1:1) gave 1.22 g of product, as a mixture of geometric isomers.

$^1$H NMR (CDCl$_3$) δ: 0.17 (s, 6H), 0.98 (s, 9H), 2.48 (s, 3H), 5.02 (m, 2H).

Step D

To a stirred, warm solution of 1.19 g (3.13 mmol) of acetate, prepared in the previous step, in 20 mL EtOH was added dropwise 0.77 mL (3.85 mmol) of a 5N solution of sodium hydroxide in water. The resulting dark solution was stirred further for 5 minutes and then partitioned between EtOAc, ice, 1N HCl, and brine. The organic phase was separated, washed with brine, dried over $Na_2SO_4$, filtered, evaporated, and dried in vacuo. Purification by PLC eluted with $CH_2Cl_2$ gave 890.0 mg of product, as a mixture of geometric isomers.

$^1$H NMR (CDCl$_3$) δ: 0.15 (s, 6H), 0.96 (s, 9H), 4.98 (m, 2H), 5.18 & 5.22 (2s's, 1-OH), 6.68–8.1 (m, 8H).

Preparative Example 12

Preparation Of 4-hydroxy-7-t-butyldimethylsiloxymethyl-fluoren-9-one

Step A

Preparation of 2-Methoxy-6-carbomethoxy-4'-t-butyldiphenylsilyloxymethylbiphenyl Using the procedure described Preparative Example 5, 10.0 g (34.2 mmol) of methyl-2-iodo-3-methoxybenzoate (prepared as outlined by W. M. Stanley, E. McMahon, and R. Adams, *J. Amer. Chem. Soc.* 1933, 55, 706) was refluxed for 5 hours to give after chromatography on silica gel with $CH_2Cl_2$-hexanes (2:1) 12.1 g of the title compound.

$^1$H NMR (CDCl$_3$) δ: 1.14 (s, 9H), 3.57 (s, 3H), 3.78 (s, 3H), 7.1–7.77 (m, ArH).

Step B

Preparation of 2-Methoxy-4'-hydroxymethylbiphenyl-6-carboxylic acid

A stirred mixture of 6.0 g (11.7 mmol) of biphenyl derivative prepared in Step A and 4.7 mL of 5N NaOH in 100 mL of EtOH was refluxed in an inert atmosphere of nitrogen for 4 hours. The mixture was partitioned between EtOAc, ice, 2N HCl, and the organic phase was separated, washed with brine, dried over $Na_2SO_4$, filtered, evaporated, and dried in vacuo. Upon addition of a little $CH_2Cl_2$ the product crystallized and after the addition of some hexanes 1.95 g of the product was collected by filtration and dried in vacuo.

$^1$H NMR (d$_6$-acetone) δ: 3.74 (s, 3H), 4.64 (s, 2H), 7.17–7.44 (m, 7ArH).

Step C

Preparation of 4-Methoxy-7-chloromethyl-fluoren-9-one

To a stirred suspension of 2.0 g (7.74 mmol) of acid prepared in Step B in 40 mL of sieve-dried $CH_2Cl_2$ at 0° C. was added all at once 3.55 g (17.0 mmol) of phosphorous pentachloride and the mixture was stirred further for 5 minutes, and then for 1 hour with the ice-water bath removed. The homogenous solution was recooled to 0° C., and 1.55 g (11.6 mmol) of AlCl$_3$ was added all at once. The resulting mixture was stirred further for 0.5 hour and then partitioned between EtOAc, ice, and brine. The organic phase was separated, washed with brine and saturated NaHCO$_3$, dried over $Na_2SO_4$, filtered, evaporated, and dried in vacuo to give 2.04 g of the title material as a yellow solid, which was used without further purification.

IR (CH$_2$Cl$_2$): 1717.5 cm$^{-1}$;

$^1$H NMR (CDCl$_3$) δ: 3.90 (s, 3H), 4.53 (s, 2H), 6.94–7.68 (m, 6ArH).

Step D

Preparation of 4-Methoxy-7-acetoxymethyl-fluoren-9-one

A mixture of 2.0 g (7.7 mmol) of material prepared in Step C and 1.52 g (15.5 mmol) of potassium acetate in 30 mL of DMF was stirred at 100° C. under nitrogen for 36 minutes. The cooled mixture was partitioned between EtOAc and ice-water and the organic phase was separated, washed twice with ice-water, and then with brine, dried over $Na_2SO_4$, filtered, evaporated, and dried in vacuo to give 2.17 g of the title material as a yellow solid, which was used without further purification.

IR (CH$_2$Cl$_2$): 1742, 1718 cm$^{-1}$;

$^1$H NMR (CDCl$_3$) δ: 2.12 (s, 3H), 3.99 (s, 3H), 5.10 (s, 2H), 7.04–7.81 (m, 6ArH).

Step E

Preparation of 4-Methoxy-7-hydroxymethyl-fluoren-9-one

A stirred mixture of the acetate prepared above and 3.07 mL (15.4 mmol) of 5N NaOH in 100 mL of EtOH was refluxed under nitrogen for 10 minutes. The cooled mixture was partitioned between EtOAc, ice-water and 2N HCl, and the organic phase was separated, washed with brine, dried over $Na_2SO_4$, filtered, evaporated, and dried in vacuo to give 2.07 g of the title material as a yellow solid, which was used without further purification.

$^1$H NMR (CDCl$_3$) δ: 3.96 (s, 3H), 4.68 (s, 2H), 7.01–7.77 (m, 6ArH).

Step F

Preparation of 4-Methoxy-7-formyl-fluoren-9-one

To a stirred suspension of 1.85 g (7.69 mmol) of carbinol from Step E in 50 mL CH$_2$Cl$_2$ was added 270.1 mg (0.769 mmol) of tetrapropylammonium perruthenate. After stirring for 5 minutes, 1.35 g (11.5 mmol) of solid N-methyl-morpholine-N-oxide was added all at once, and the resulting mixture stirred further for 5 minutes. The dark solution was passed over a column of florisil eluted with CH$_2$Cl$_2$-EtOAc (10:1) to give 1.42 g of the title aldehyde as a yellow solid.

IR (CH$_2$Cl$_2$): 1720, 1698 cm$^{-1}$;

$^1$H NMR (CDCl$_3$) δ: 4.02 (s, 3H), 7.09–8.1 (m, 6ArH), 10.0 (s, 1H).

Step G

Preparation of 4-Hydroxy-7-formyl-fluoren-9-one

A stirred mixture of the methylether from the previous step and 30 mL of 48% HBr in 15 mL of acetic acid was heated at 130° C. under nitrogen for 7 hours. The cooled mixture was poured onto ice-water and the separated product collected by suction filtration, washed well with water, and dried in vacuo to give 0.94 g of the title compound.

$^1$H NMR (d$_6$-acetone) δ: 7.18–8.15 (m, 6ArH), 9.8 (s, 1-OH), 10.07 (s,1-CHO).

Step H

Preparation of 4-Hydroxy-7-hydroxymethyl-fluoren-9-one

A stirred mixture of 405.2 mg (1.8 mmol) of aldehyde prepared in Step G and 804.3 mg (3.8 mmol) of sodium triacetoxyborohydride in 27 mL of anhydrous THF was refluxed under nitrogen for 1 hour. The cooled mixture was partitioned between EtOAc, ice-water and saturated NaHCO$_3$, and the organic phase was separated, washed with brine, dried over Na$_2$SO$_4$, filtered, evaporated, and dried in vacuo. Purification by PLC with CH$_2$Cl$_2$-EtOAc (2:1) yielded 303.7 mg of the crystalline, title product.

$^1$H NMR (d$_6$-acetone) δ: 4.66 (s,2H), 7.08–7.86 (m, 6ArH), 9.38 (s, 1-OH).

Step I

A mixture of 332.2 mg (1.47 mmol) of the diol from Step H, 243.5 mg (1.61 mmol) of t-butyldimethylchlorosilane, and 120 mg (1.76 mmol) of imidazole in 8 mL of sieve dried DMF was stirred at 0° C. for 45 minutes. The mixture was partitioned between EtOAc, ice-water and 2N HCl, and the organic phase was separated, washed twice with ice-water, and then with brine, dried over Na$_2$SO$_4$, filtered, evaporated, and dried in vacuo. Purification by PLC using CH$_2$Cl$_2$-EtOAc (50:1) gave 447.4 mg of the title material.

$^1$H NMR (d$_6$-acetone) δ: 0.14 (s, 6H), 0.95 (s, 9H), 4.81 (s,2H), 7.08–7.86 (m, 6ArH), 9.35 (bs, 1-OH).

Preparative Example 13

Preparation of 4-hydroxy-7-(3-t-butyldimethylsilyloxypropyl)-fluoren-9-one

Step A

Preparation of 4-Acetoxy-7-formyl-fluoren-9-one

To a stirred suspension of 1.53 g (6.83 mmol) of 4-hydroxy-7-formyl-fluoren-9-one, prepared in Step G of Prepartive Example 12, in 25 mL THF at 0° C. was added 1.24 mL (8.88 mmol) of triethylamine and 0.58 mL (8.2 mmol) of acetyl chloride. The mixture was stirred further for 0.5 hour and then partitioned between EtOAc, ice, 1N HCl, and brine. The organic phase was separated, washed with brine, dried over Na$_2$SO$_4$, filtered, evaporated, and dried in vacuo. Purification by chromatography on silica gel using methylene chloride as eluant gave 1.46 g of the title compound.

IR (CH$_2$Cl$_2$): 1772, 1724, 1702, 1618,1606 cm$^{-1}$;

$^1$H NMR (CDCl$_3$) δ: 2.48 (s, 3H), 7.38–8.15 (m, 6ArH), 10.0 (s, 1H).

Step B

Preparation of 4-Acetoxy-7-(E-2-carbomethoxyvinyl)-fluoren-9-one

A mixture of 1.46 g (5.49 mmol) of aldehyde, prepared in Step A, and 2.02 g (6.04 mmol) of methyl-(triphenylphosphoranylidene)-acetate in 25 mL of methylene chloride was stirred at room temperature for 1 hour, during which time product precipitation was progressive. Ether-hexanes (2:1, 20 mL) was added and the yellow solid was collected by suction filtration, washed with 60 mL of ether-hexanes (2:1), and dried in vacuo to give 1.43 g of the title material.

$^1$H NMR (CDCl$_3$) δ: 2.48 (s, 3H), 3.82 (s, 3H), 6.49 (d, J=16 Hz, 1H), 7.30–7.87 (m, 6ArH), 7.68 (d, J=16 Hz, 1H).

Step C

Preparation of 4-Acetoxy-7-(2-carbomethoxyethyl)-fluoren-9-one

The material prepared above in Step B, 1.11 g (3.45 mmol) and 267 mg of 5% Rh/C in 60 mL methylene chloride and 12 mL methanol was stirred under balloon pressure of hydrogen for 5 hours. The catalyst was removed by filtration through celite, washed well with methylene chloride, and the filtrate evaporated and dried in vacuo to give 1.1 g of product which was used without further purification.

$^1$H NMR (CDCl$_3$) δ: 2.46 (s, 3H), 2.65 (t, J=7.5 Hz, 2H), 2.98 (t, J=7.5 Hz, 2H), 3.67 (s, 3H), 7.23–7.56 (m, 6ArH).

Step D

Preparation of 2-(4-Hydroxy-7-fluoren-9-one) propionic acid

A stirred mixture of 1.27 g (3.92 mmol) of ester, prepared in Step C above, and 2.43 mL (12.2 mmol) of 5N NaOH in 30 mL of EtOH was refluxed under nitrogen for 70 minutes. The cooled mixture was partitioned between EtOAc, ice, 2N HCl, and brine, and the organic phase was separated, washed with brine, dried over Na$_2$SO$_4$, filtered, evaporated, and dried in vacuo to give 1.04 g of the title acid.

$^1$H NMR (d$_6$-acetone) δ: 2.67 (t, J=7.5 Hz, 2H), 2.97 (t, J=7.5 Hz, 2H), 7.08–7.80 (m, 6ArH), 9.37 (s, bs, 1H).

Step E

Preparation of 4-Hydroxy-7-(3-hydroxypropyl)-fluoren-9-ol

To a stirred suspension of the acid (905.1 mg, 3.38 mmol), prepared above in Step D, in 30 mL of anhydrous THF at ambient temperature was added cautiously 10.1 mL of 1M borane-THF in THF. The resulting mixture was stirred further for 2 hours and carefully quenched with methanol. The mixture was evaporated and the residue partitioned between EtOAc, ice, saturated NaHCO$_3$, and brine, and the organic phase was separated, washed with brine, dried over Na$_2$SO$_4$, filtered, evaporated, and dried in vacuo to give 0.96 g of the title triol.

$^1$H NMR (d$_6$-acetone) δ: 1.85 (m, 2H), 2.74 (t, J=7.4 Hz, 2H), 3.60 (t, J=7.4 Hz, 2H),5.49 (d, J=6.1 Hz, 1H), 6.83–7.91 (m, 6ArH), 8.88 (s, 1H).

Step F

Preparation of 4-Hydroxy-7-(3-hydroxypropyl)-fluoren-9-one

A stirred mixture of 870 mg (3.38 mmol) of triol, prepared in Step E, and 958 mg (13.5 mmol) of manganese dioxide in 20 mL of acetone was refluxed for 17 hours. The cooled mixture was filtered through celite, washed well with acetone, and the filtrate evaporated and dried in vacuo to give 832.2 mg of the title compound, as a brick-red solid.

$^1$H NMR (d$_6$-acetone) δ: 1.85 (m, 2H), 2.74 (t, J=7.4 Hz, 2H), 3.59 (m, 2H), 7.06–7.79 (m, 6ArH), 9.30 (s,1H).

Step G

A mixture of 832.2 mg (3.28 mmol) of diol, prepared in Step F above, 543.2 mg (3.6 mmol) of t-butyldimethylchlorosilane, and 267.7 mg (3.9 mmol) of imidazole in 10 mL sieve-dried DMF was stirred at 0° C. for 45 minutes. The mixture was partitioned between EtOAc, ice, and 2N HCl, and the organic phase was separated, washed twice with ice-water and then with brine, dried over Na$_2$SO$_4$, filtered, and evaporated. The residue was purified by silica gel chromatography using an elution gradient of methylene chloride-ethyl acetate (50:1 to 10:1) to give 1.05 g of the title product.

$^1$H NMR (CDCl$_3$) δ: 0.04 (s, 6H), 0.89 (s, 9H), 1.84 (m, 2H), 2.68 (t, J=6.3 Hz, 2H), 3.62 (t, J=6.3 Hz, 2H), 5.25 (bs, 1H),5.7 (d, J=15 Hz, 1H), 6.98–7.61 (m, 6ArH)

Preparative Example 14

Preparation of 4-hydroxy-7-(3-t-butyldimethylsilyloxpropyl)-9-carbomethoxy-fluorylidene A stirred mixture of 110.4 mg (0.3 mmol) of fluorenone derivative prepared in Preparative Example 8 and 250.8 mg (0.75 mmol) of methyl-(triphenylphosphoranylidene)-acetate in 3 mL of p-xylene was refluxed under nitrogen for 21 hours. The cooled mixture was evaporated and the residue purified by PLC with $CH_2Cl_2$-EtOAc (50:1) to give 90 mg of the title compound as a mixture of geometric isomers.

$^1$H NMR ($CDCl_3$) δ: 0.07 (s, 6H), 0.92 (s, 9H), 1.87 (m, 2H), 2.73 (m, 2H), 3.65 (t, 2H), 3.87 (s, 3H), 6.71–8.74 (m, 7H).

Preparative Example 15

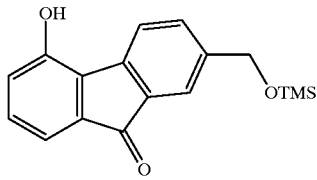

To a stirred solution of 400.0 mg (1.77 mmoles) of the diol obtained in preparative example 12, step H, in 8.0 ml of sieve dried DMF, cooled to 0° C., is added imidazole (144 mg, 2.12 mmoles) and neat chlorotrimethysilane (0.247 ml, 1.977 mmoles). The solution is stirred for 1 hr., diluted with ethyl acetate and washed with ice-water, 0.50 ml of 2.0N aq. HCl and saturated brine. The organic phase is dried over anhydrous sodium sulfate, filtered and conc. in vacuo to dryness. Purification by silica gel plate layer chormatography gives the product.

Preparative Example 16

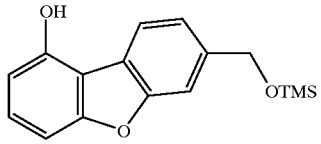

To a stirred solution of 150.0 mg (0.703 mmoles) of the diol obtained in preparative example 4, step I, in 4.0 ml of sieve dried DMF, cooled to 0° C., is added imidazole (57 mg, 0.843 mmoles) and neat chlorotrimethylsilane (0.93 ml, 0.733 mmoles). The solution is stirred for 1 hr., diluted with ethyl acetate and washed with ice-water, 0.5 ml of 2.0N aq. HCl and saturated brine. The organic phase is dried over anhydrous sodium sulfate, filtered and conc. in vacuo to dryness. Purification by silica gel plate layer chormatography gives the product.

Preparative Example 17

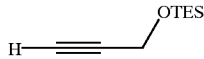

To a stirred solution of commercially available propargyl alcohol (5.0 g, 35.72 mmoles) in 50 ml of sieve dried N,N-dimethylformamide, cooled to 0° C., was added imidazole (668 mg, 9.83 mmoles) followed by neat triethylsilyl chloride (16.2 ml, 96.21 mmoles). The cooling bath was removed and the mixture was stirred at ambient temperature for 10 min. The resulting solution was diluted with ethyl acetate, washed with water-ice, 0.5M aq. sodium bicarbonate and saturated brine. The organic phase was dried over anhydrous sodium sulfate, filtered and concentrated in vacuo to give a colorless oil. Fractional distillation gave 3.03 g (51%) (b.p. 57° C.–61° C., 3.7 mm); of pure product as a colorless oil.

$^1$H NMR ($CDCl_3$) δ: 0.65 (q, 6H), 0.95 (t, 9H), 2.43 (t, 1H), 4.35 (dd, 2H).

Preparative Example 18

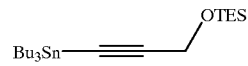

To a stirred solution of product obtained in preparative example 14 (3.03 g, 18.15 mmoles), in 30 ml of THF, cooled to −78° C., was added n-butyllithium (8.0 ml, 19.96 mmoles) dropwise over 30 min. The reaction was allowed to warmed to −20° C. and was stirred for 1 hour. Neat tri-n-butyltin chloride (5.89 ml, 21.78 mmoles) was then added dropwise over 30 min. The reaction mixture was warmed to 0° C. and stirred for 1 hr. The resulting dark solution was diluted with ethyl acetate, washed with water-ice and sat. brine. The organic phase was dried over anhydrous sodium sulfate, filtered and concentrated in vacuo to give a brown oil. Flash chromatography with 200–400 mesh florisil (100:1 florisil: product, eluent: 9:1 hexanes:dichloromethane) gave 6.12 g (74%) of the product as a colorless oil.

$^1$H NMR ($CDCl_3$) δ: 0.64 (q, 6H), 0.91 (t, 6H), 1.02 (t, 18H), 1.31 (m, 6H), 1.72 (m, 6H), 4.34 (s, 2H).

EXAMPLE 1

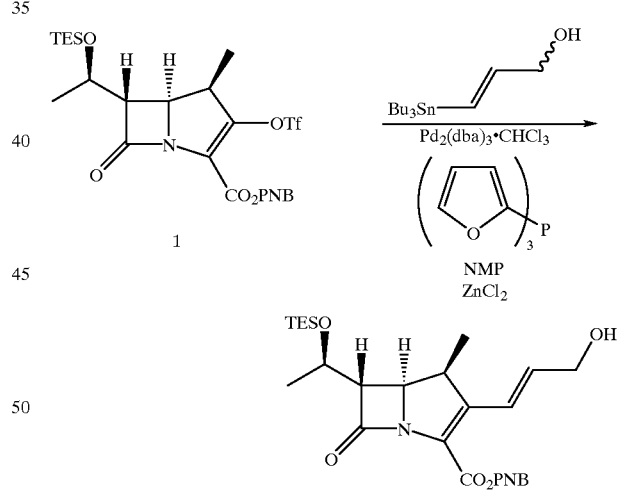

A mixture of 2-yl-carbapenem triflate 1 (200 mg, 0.329 mmoles), a 2:1 mixture of (E)-trans: (Z)-cis vinylstannanes (0.144 ml 0.493 mmoles), prepared as described in Jung, M. E.; Light, L. A. *Tetrahedron Lett.* 1982, 23, 3851, palladium dibenzylidineacetone chloroform complex (17 mg, 0.0165 mmoles) and tris-trifuryl phosphine (7.6 mg, 0.0329 mmoles) was combined and dissolved in 4.0 ml of N-methylpyrrolidinone, at ambient temperature. A 1.0 M etheral solution of zinc chloride (0.0329 ml, 0.0329 mmoles) was then added to the solution and the mixture was stirred for 6 hrs. The mixture was diluted with ethyl acetate, washed with water-ice and sat. brine. The organic phase was dried over anhydrous sodium sulfate, filtered and conc. in vacuo to give a brown oil. Silica gel plate layer chromatography (4×1000 microns, eluent: 1:1 ethyl acetate:hexanes) yielded 103 mg (60%) of the desired product as a colorless oil.

$^1$H NMR (CDCl$_3$) δ: 0.58 (m, 6H), 0.94 (t, 9H), 1.22 (d, 3H), 1.29 (d, 3H), 3.23 (dd, 1H), 3.37 (d, 1H), 4.19 (dd, 1H), 4.21 (m, 1H), 4.32 (dd, 2H), 5.26–5.48 (q, 2H), 6.18 (dd, 1H), 7.27 (d, 1H), 7.68 (d, 2H), 8.22 (d, 2H).

EXAMPLE 2

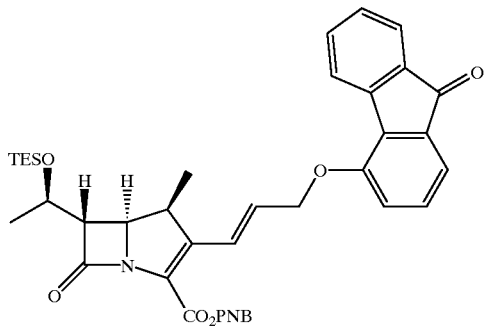

The carbinol (60 mg, 0.116 mmoles) obtained from example 1, along with commercially available 4-hydroxyfluoren-9-one (25 mg, 0.128 mmoles) and triphenylphosphine (34 mg, 0.128 mmoles) were combined, in 2.0 ml of anhydrous THF and cooled to 0° C. Neat diisopropylazodicarboxylate (0.035 ml, 0.179 mmoles) was added and the mixture was stirred for 20 min. The resulting solution was concentrated in vacuo to give an orange oil. Silica gel plate layer chromatography (1×1000 microns; eluent: 4:1 hexanes:ethyl acetate) gave 57 mg (71%) of a yellow oil.

$^1$H NMR (CDCl$_3$) δ: 0.35 (q, 6H), 0.93 (t, 9H), 1.21 (t, 6H), 3.28 (dd, 1H), 3.43 (m, 1H), 4.28 (m, 2H), 4.86 (dd, 2H), 5.21–5.49 (ABq, 2H), 6.24 (dt, 1H), 7.04 (d, 1H), 7.14 (t, 1H), 7.25–7.34 (m, 3H), 7.45 (t, 1H), 7.63 (m, 3H), 7.89 (d, 1H), 8.22 (d, 2H).

EXAMPLE 3

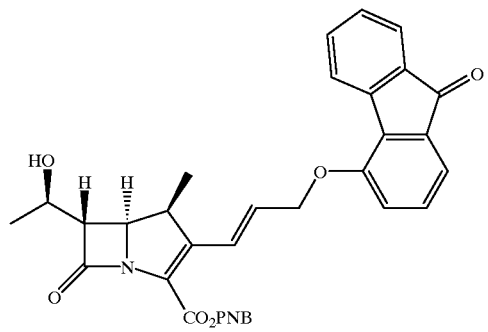

To a stirred solution of 63 mg (0.0908 mmoles) of the product obtained in example 2, in 1.0 ml of a 2:1 mixture of THF: H$_2$O, cooled to 0° C., was added 1.0 N aq. HCl (0.045 ml, 0.045 mmoles) and the reaction was stirred at ambient temperature for 2.0 hrs. The reaction mixture was diluted with ethyl acetate and washed with water-ice, 5% aq. sodium bicarbonate and saturated brine. The organic phase was dried over sodium sulfate, filtered and conc. in vacuo to give an orange residue. Purification by silica gel plate layer chromatography (1×1000 microns, eluent: 7:3 ethyl acetate:hexanes) gave 43 mg (82%) of product as an orange solid.

$^1$H NMR (CDCl$_3$) δ: 1.26 (d, 3H), 1.37 (d, 3H), 3.29 (dd, 1H), 3.47 (m, 1H), 4.25 (m, 2H), 4.84 (dd, 2H), 5.22–5.52 (ABq, 2H), 6.27 (dt, 1H), 7.00 (d, 1H), 7.24 (m, 3H), 7.42 (t, 1H), 7.56 (m, 3H), 7.88 (d, 1H), 8.21 (d, 2H).

EXAMPLE 4

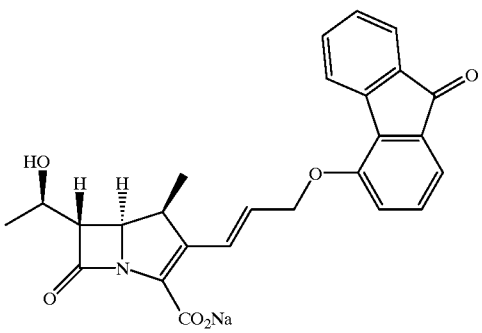

To a stirred solution of 23 mg (0.0396 mmoles) of the product obtained in example 3, in 1.5 ml of a 2:1 mixture of THF: H$_2$O, cooled to 0° C., was added 1.0 N aq. sodium bicarbonate (0.044 ml, 0.044 mmoles) and 5% Rh/C (2.3 mg) catalyst. The cooling bath was removed and the reaction mixture was stirred under a balloon of hydrogen, at ambient temperature for 45 min. The reaction mixture was filtered through celite and concentrated in vacuo to give an orange residue. Reverse phase silca gel plate layer chromatography (1×1000 microns, eluent: 7:3 H$_2$O:acetonitrile) gave after lyophilization 6.2 mg (33%) of desired product as an orange solid.

$^1$H NMR (2:1 D$_2$O: CD$_3$CN) δ: 1.43 (d, 3H), 1.58 (d, 3H), 3.61 (dd, 1H), 3.72 (m, 1H), 4.43 (dd, 1H), 4.48 (p, 1H), 5.47 (d, 2H), 6.49 (dt, 1H), 7.61–7.65 (m, 4H), 7.78 (d, 1H), 7.92 (m, 2H), 8.21 (d, 1H).

EXAMPLE 5

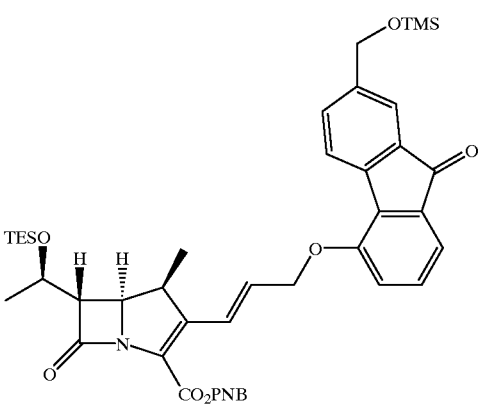

The carbinol (60 mg, 0.116 mmoles) obtained from example 1, along with 39 mg (0.116 mmoles) of the product obtained from preparative example 16, and triphenylphosphine (34 mg, 0.128 mmoles) is combined, in 2.0 ml of anhydrous THF and cooled to 0° C. Neat diisopropylazodicarboxylate (0.035 ml, 0.179 mmoles) is added and the mixture is stirred for 20 min. The resulting solution is concentrated in vacuo to give a residue which is purified by silica gel plate layer chromatography to give the product.

EXAMPLE 6

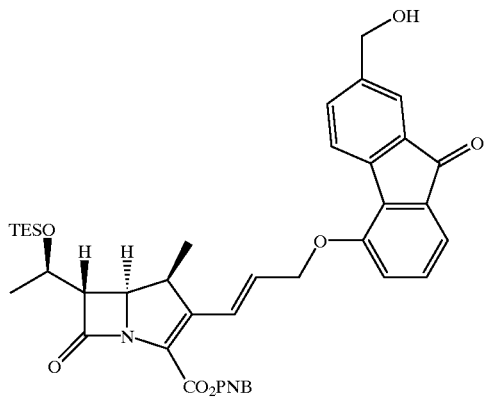

To a stirred solution of 170 mg (0.213 mmoles) of the product obtained in example 5, in 2.0 ml of anhydrous THF, cooled to 0° C., is added sequentially acetic acid (0.018 ml, 0.320 mmoles) and a 1.0 M THF solution of tetrabutylammonium fluoride (0.234 ml, 0.234 mmoles). The mixture is stirred for 1 hr., diluted with ethyl acetate, washed with water-ice, saturated aq. sodium bicarbonate and sat. brine. The organic phase is dried over anhydrous sodium sulfate, filtered and concentrated in vacuo to provide the crude product. Purification by silica gel plate layer chromatography gives the product.

EXAMPLE 7

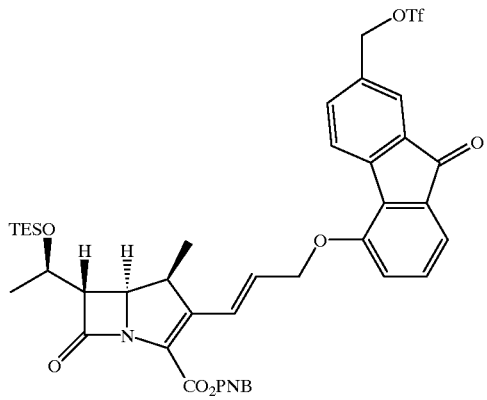

To a stirred solution of 80 mg (0.110 mmoles) of the product obtained in example 6, in 1.0 ml of anhydrous THF, cooled to −20° C., is added neat 2,6-lutidine (0.0134 ml, 0.115 mmoles) and the solution is stirred for 5 min. Neat triflic anhydride (0.020 ml, 0.121 mmoles) is then added and the mixture was stirred for 15 min. The reaction mixture is diluted with ethyl acetate, washed with water-ice, 0.050 ml of 2.0N aq. HCl and saturated brine. The organic phase is dried over anhydrous sodium sulfate, filtered and concentrated in vacuo to give the product used without purification.

EXAMPLE 8

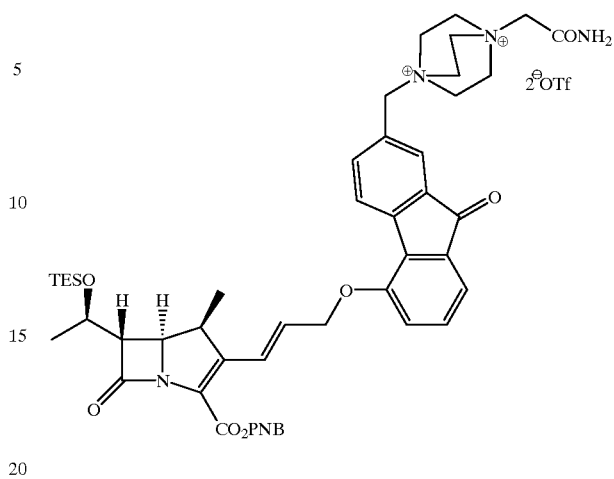

To a stirred solution of 75 mg (0.0876 mmoles) of freshly prepared product obtained from example 7, in 1.0 ml of sieve dried acetonitrile, at ambient temperature, is added 4-carbamoylmethyl-1,4-diazoniabicyclo-{2.2.2}-octyl triflate (28 mg, 0.0876 mmoles). The solution is stirred for 30 min., concentrated in vacuo to dryness and redissolved in 1.0 ml of acetone. The solution is diluted with 8.0 ml of diethyl ether to give a milky suspension which is centrifuged and dried to give the product.

EXAMPLE 9

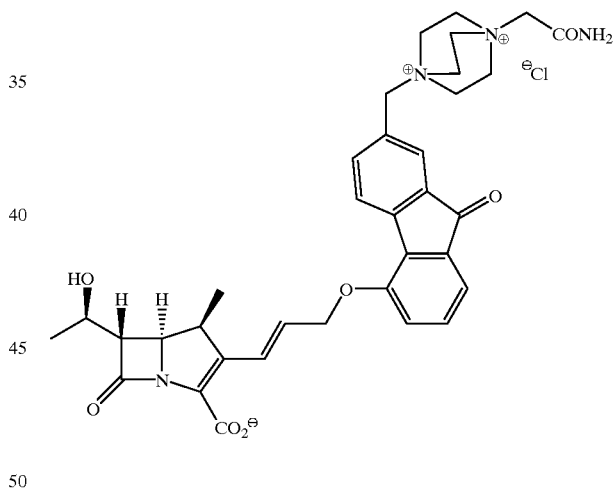

To a stirred solution of 50 mg (0.0437 mmoles) of the product obtained in example 8, in a 2:1 mixture of THF:H$_2$O, cooled to 0° C., is added 1.0 N aq. HCl (0.0437 ml, 0.0437 mmoles). The cooling bath is removed and the reaction is stirred at ambient temperature for 1.5 hrs. The mixture is cooled to 0° C. and neutralized with 1.0N aq. sodium bicarbonate (0.0437 ml, 0.0437 mmoles) and charged with 5% Pt/C (5.0 mg) catalyst. The suspension is stirred vigorously, under a balloon of hydrogen, at ambient temperature for 30 min. The mixture is filtered through celite, washed with ethyl acetate and concentrated in vacuo to dryness. The resulting residue is dissolved in 2.0 ml of deionized water and is passed through a column containing Macro prep ion exchange resin and eluted with a 5% aq. brine solution. The resulting solution is subsequently desalted using amberchrom CG-161 resin to give after lyophilization the product.

EXAMPLE 10

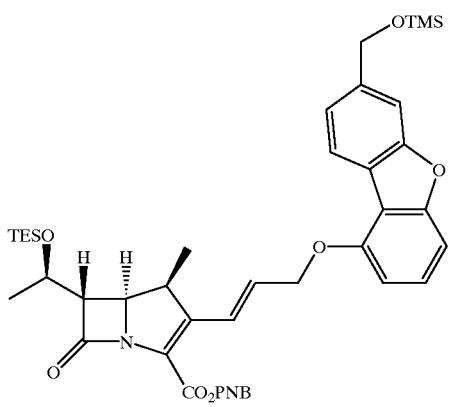

Using the procedure described in example 5, the carbinol (90 mg, 0.126 mmoles) obtained from example 1, along with 43 mg (0.151 mmoles) of the product obtained from preparative example 19, and triphenylphosphine (40 mg, 0.151 mmoles) is combined, in 2.0 ml of anhydrous THF and is treated with neat diisopropylazodicarboxylate (0.030 ml, 0.151 mmoles). Purification by silica gel plate layer chromatography gives the product.

EXAMPLE 11

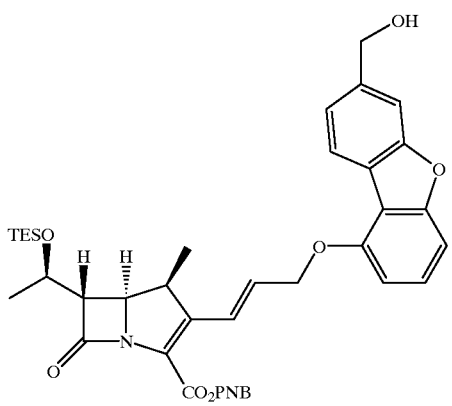

Using the procedure described in example 6, a stirred solution of 130 mg (0.165 mmoles) of the product obtained in example 10, in 2.0 ml of anhydrous THF, cooled to 0° C., is treated with acetic acid (0.014 ml, 0.248 mmoles) and a 1.0 M THF solution of tetra-butylammonium fluoride (0.182 ml, 0.182 mmoles). Purification by silica gel plate layer chromatography gives the product.

EXAMPLE 12

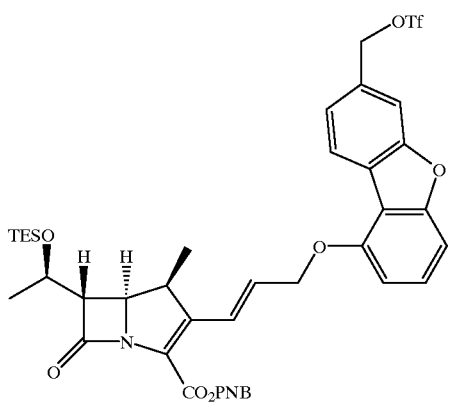

Using the procedure described in example 7, a stirred solution of 75 mg (0.105 mmoles) the product obtained in example 11, in 1.0 ml of anhydrous THF, cooled to −20° C., is treated with neat 2,6-lutidine (0.0128 ml, 0.110 mmoles) and triflic anhydride (0.021 ml, 0.126 mmoles). The product is used without purification.

EXAMPLE 13

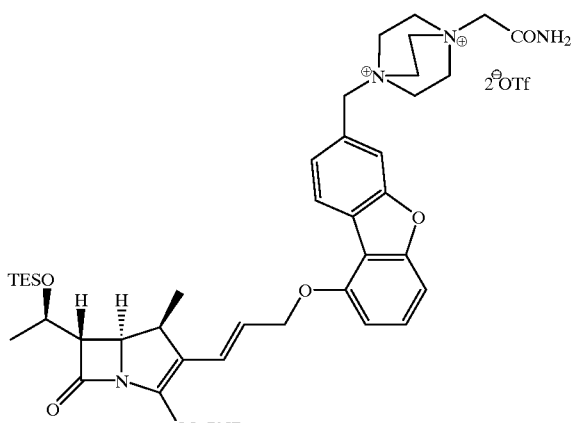

Using the procedure described in example 8, a stirred solution of 90 mg (0.106 mmoles) of freshly prepared product obtained from example 12, in 2.0 ml of sieve dried acetonitrile, at ambient temperature, is reacted with 4-carbamoylmethyl-1,4-diazoniabicyclo-{2.2.2}-octyl triflate (34 mg, 0.0876 mmoles). Precipitation from acetone/ether gives the product.

EXAMPLE 14

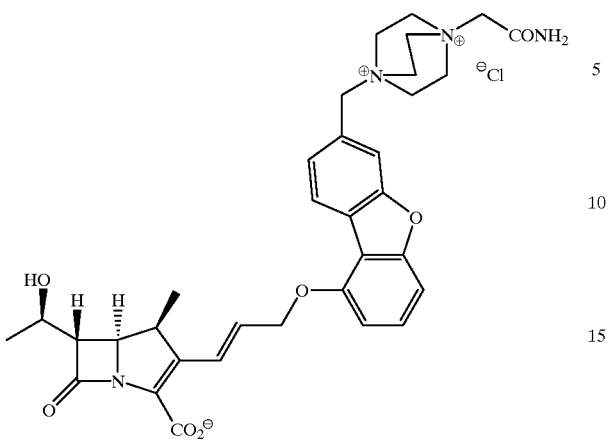

Using the procedure described in example 9, a stirred solution of 50 mg (0.0442 mmoles) of the product obtained in example 8, in 1.0 ml of a 2:1 mixture of THF-H$_2$O, cooled to 0° C., is treated 1.0 N aq. HCl (0.0442 ml, 0.0442 mmoles) and neutralized with 1.0N aq. sodium bicarbonate (0.0442 ml, 0.0442 mmoles). The solution is hydrogenated using 5% Pt/C (5.0 mg), treated with Macro prep ion exchange resin and desalted using amberchrom CG-161 resin to give after lyophilization the product.

EXAMPLE 15

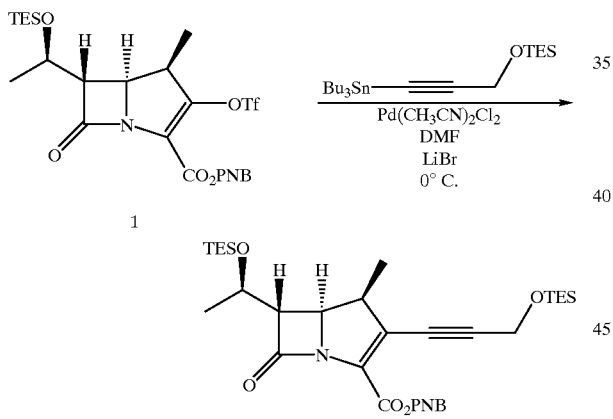

To a stirred solution of carbapenem 2-yl-triflate 1 (100 mg, 0.164 mmoles) and propargylstannane (112 mg, 0.246 mmoles) obtained in preparative example 19, in 2 mL of anhydrous N,N-dimethylformamide, at 0° C., was added lithium bromide (28 mg, 0.328 mmoles) and bis-acetonitrilepalladium (II) chloride (2.1 mg, 0.0082 mmoles). The reaction mixture was stirred for 1 hr, diluted with ethyl acetate and washed with water-ice and saturated brine. The organic phase was dried over anhydrous sodium sulfate, filtered and concentrated in vacuo to give an orange oil. Silica gel plate layer chromatography (2×1000 microns; eluent: 4:1 hexane ethyl acetate) gave 70 mg (68%) of the desired product as a pale yellow oil.

$^1$H NMR (CDCl$_3$) δ: 0.59 (m, 12H), 0.73 (m, 18H), 1.24 (d, 3H), 1.26 (d, 3H), 3.18 (m, 1H), 3.20 (dd, 1H), 4.12 (d, 1H), 4.25 (dd, 1H), 4.53 (s, 2H), 5.28–5.49 (q, 2H), 7.65 (d, 2H), 8.21 (d, 2H).

EXAMPLE 16

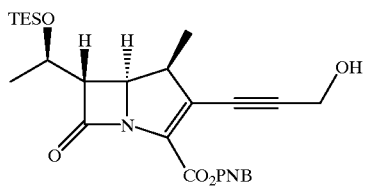

To a stirred solution of 77 mg (0.122 mmoles) of the product obtained in example 1, in 1.0 ml of anhydrous THF, at 0° C., was added sequentially acetic acid (11 ml, 0.183 mmoles) and a 1.0 M THF solution of tetra-butylammonium fluoride (0.122 ml, 0.122 mmoles). The mixture was stirred for 1 hr., diluted with ethyl acetate, washed with water, saturated aq. sodium bicarbonate and saturated brine. The organic phase was dried over sodium sulfate, filtered and concentrated in vacuo to give a yellow solid. Silica gel plate layer chromatography (1×1000 microns; eluent: 1:1 hexanes:ethyl acetate) gave 33 mg (53%) of a yellow crystalline solid.

$^1$H NMR (CDCl$_3$) δ: 0.57 (q, 6H), 0.90 (t, 9H), 1.22 (t, 6H), 1.74 (t, 1H), 3.16 (m, 1H), 3.23 (dd, 1H), 4.23–4.32 (m, 2H), 4.48 (d, 2H), 5.26–5.48 (q, 2H), 7.64 (d, 2H), 8.21 (d, 2H).

EXAMPLE 17

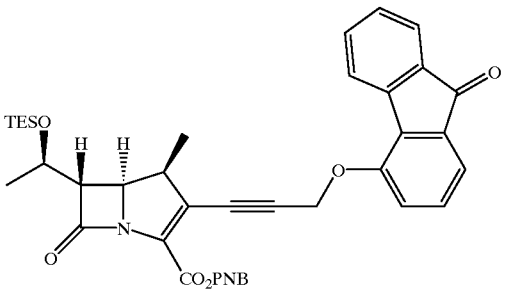

Using the procedure described in example 2, the carbinol (69 mg, 0.134 mmoles) obtained from example 16, along with commercially available 4-hydroxyfluoren-9-one (29 mg, 0.148 mmoles) and triphenylphosphine (39 mg, 0.148 mmoles) were combined in 2.0 ml of anhydrous THF and cooled to 0° C. and treated with diisopropylazodicarboxylate (0.029 ml, 0.148 mmoles). Silica gel plate layer chromatography (1×1000 microns; eluent: 4:1 hexanes:ethyl acetate) gave 63 mg (68%) of an orange oil.

$^1$H NMR (CDCl$_3$) δ: 0.53 (q, 6H), 0.89 (t, 9H), 1.14 (d, 3H), 1.27 (t, 3H), 3.12 (m, 1H), 3.29 (dd, 1H), 4.20 (p, 1H), 4.28 (dd, 1H), 5.06 (s, 2H), 5.16–5.37 (ABq, 2H), 7.14 (d, 1H), 7.21 (m, 2H), 7.31 (d, 1H), 7.41 (t, 1H), 7.53 (d, 2H), 7.61 (d, 1H), 7.76 (d, 1H), 8.11(d, 2H).

EXAMPLE 18

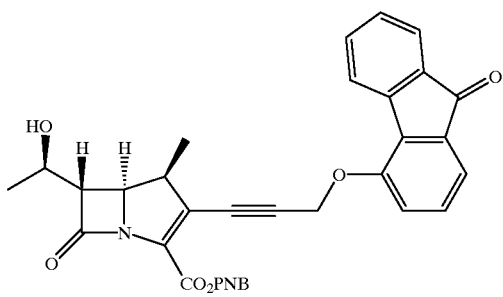

Using the procedure described in example 2, a stirred solution of 63 mg (0.0908 mmoles) of the product obtained in example 17, in a 3:1 mixture of THF: $H_2O$, cooled to 0° C., was treated with 1.0 N aq. HCl (0.045 ml, 0.045 mmoles). Silica gel plate layer chromatography (1×1000 microns, eluent: 7:3 ethyl acetate:hexanes) gave 43 mg (82%) of product as an orange solid.

$^1$H NMR (CDCl$_3$) δ: 1.16 (d, 3H), 1.29 (d, 3H), 1.78 (d, 1H), 3.17 (m, 1H), 3.33 (dd, 1H), 4.22 (m, 1H), 4.28 (dd, 1H), 5.06 (s, 2H), 5.14 (ABq, 2H), 7.13 (d, 1H), 7.22 (m, 2H), 7.34 (d, 1H), 7.41 (d, 2H), 7.51 (d, 2H), 7.58 (d, 1H), 7.76 (d, 1H), 8.10 (d, 2H).

EXAMPLE 19

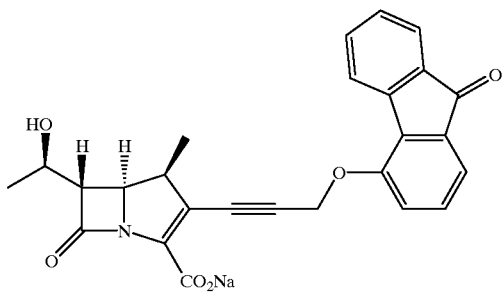

Using the procedure described in example 4, a stirred solution of 28 mg (0.0484 mmoles) the product obtained in example 18, in 1.5 ml of a 2:1 mixture of THF-$H_2O$, cooled to 0° C., was added 1.0 N aq. sodium bicarbonate (0.053 ml, 0.053 mmoles). The mixture was hydrogenated using 5% Rh/C (1.0 mg) catalyst to give an orange residue. Purification by reverse phase silica gel plate layer chromatography (1×1000 microns, eluent: 7:3 $H_2O$:acetonitrile) gave after lyophilization 9.3 mg (41%) of desired product as an orange solid.

$^1$H NMR (2:1 $D_2O$: $CD_3CN$) δ: 1.34 (d, 3H), 1.51 (d, 3H), 3.32 (m, 1H), 3.66(dd, 1H), 4.46 (m, 2H), 5.50 (s, 2H), 7.13 (t, 1H), 7.62–7.69 (m, 4H), 7.85 (d, 1H), 8.19 (d, 1H).

EXAMPLE 20

Using the prodecure described in example 5, the carbinol (72 mg, 0.139 mmoles) obtained from example 1, along with 50 mg (0.167 mmoles) of the product obtained from preparative example 16, and triphenylphosphine (44 mg, 0.167 mmoles) is combined in 3.0 ml of anhydrous THF and cooled to 0° C. The mixture is treated with diisopropylazodicarboxylate (0.033 ml, 0.167 mmoles). Purification by silca gel plate layer chromatography gives the product.

EXAMPLE 21

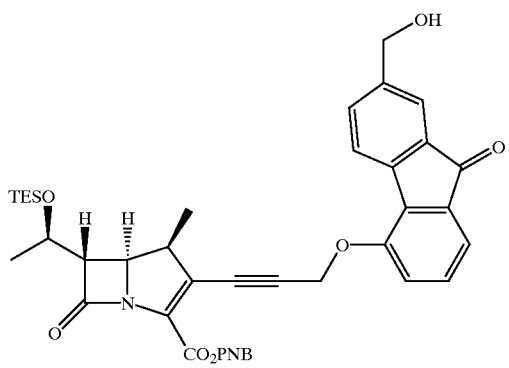

Using the prodecure described in example 6, a stirred solution of 90 mg (0.113 mmoles) of the product obtained in example 21, in 2.0 ml of anhydrous THF, cooled to 0° C., is treated sequentially with acetic acid (0.010 ml, 0.169 mmoles) and a 1.0 M THF solution of tetra-butylammonium fluoride (0.124 ml, 0.124 mmoles). Purification by silica gel plate layer chromatography gives the product.

EXAMPLE 22

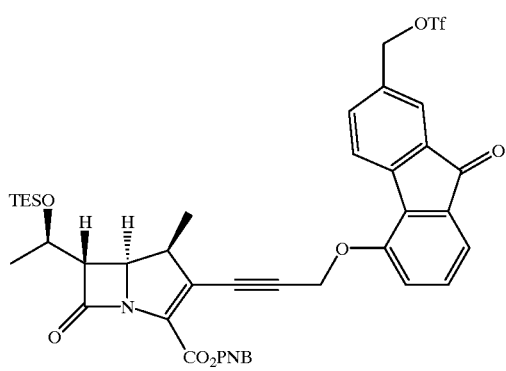

Using the prodecure described in example 8, a stirred solution of 75 mg (0.104 mmoles) of the product obtained in example 21, in 1.0 ml of anhydrous THF, cooled to −20° C., is reacted with 2,6-lutidine (0.013 ml, 0.109 mmoles) and triflic anhydride (0.019 ml, 0.114 mmoles) and the resulting product is used without purification.

EXAMPLE 23

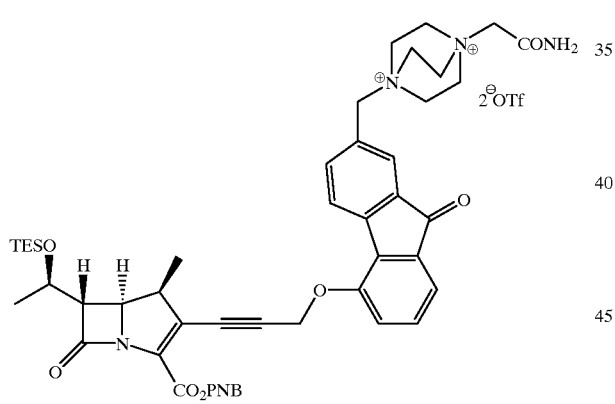

Using the prodecure described in example 8, a stirred solution of 60 mg (0.0703 mmoles) of freshly prepared product obtained from example 7, in 1.0 ml of sieve dried acetonitrile, at ambient temperature, is added 4-carbamoylmethyl-1,4-diazoniabicyclo-{2.2.2}-octyl triflate (22 mg, 0.0703 mmoles). Precipitation from acetone/ether gives the product.

EXAMPLE 24

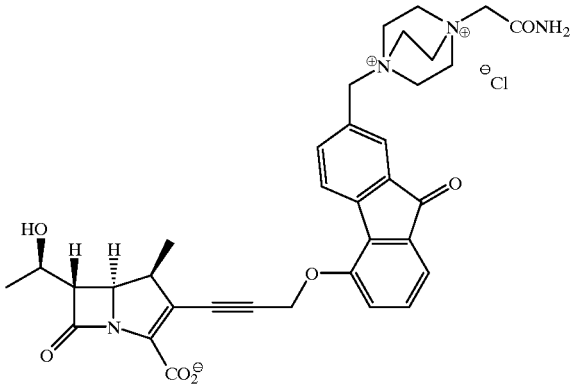

Using the procedure described in example 9, a stirred solution of 50 mg (0.0437 mmoles) of the product obtained in example 23, in 1.0 ml of a 2:1 mixture of THF-H$_2$O, cooled to 0° C., is treated 1.0 N aq. HCl (0.0437 ml, 0.0437 mmoles) and neutralized with 1.0N aq. sodium bicarbonate (0.0437 ml, 0.0437 mmoles). The mixture is hydrogenated using 5% Pt/C (5.0 mg), treated with Macro prep ion exchange resin and subsequently desalted using amberchrom CG-161 resin to give after lyophilization the product.

EXAMPLE 25

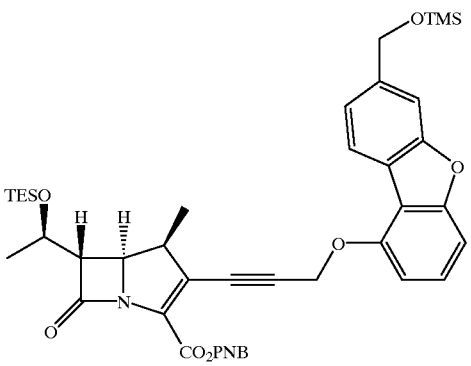

Using the prodecure described in example 5, the carbinol (83 mg, 0.161 mmoles) obtained from example 1, along with 55 mg (0.193 mmoles) of the product obtained from preparative example 17, and triphenylphosphine (51 mg, 0.193 mmoles) is combined in 3.0 ml of anhydrous THF and cooled to 0° C. The mixture is treated with diisopropylazodicarboxylate (0.038 ml, 0.193 mmoles). Purification by silica gel plate layer chromatography gives the product.

EXAMPLE 26

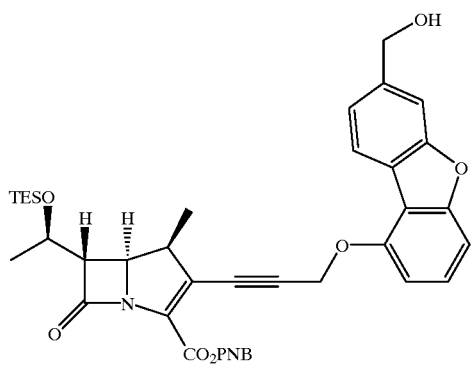

Using the prodecure described in example 6, a stirred solution of 50 mg (0.069 mmoles) of the product obtained in example 25, in 2.0 ml of anhydrous THF, cooled to 0° C., is treated sequentially with acetic acid (0.006 ml, 0.103 mmoles) and a 1.0 M THF solution of tetra-butylammonium fluoride (0.075 ml, 0.075 mmoles). Purification by silica gel plate layer chromatography gives the product.

EXAMPLE 27

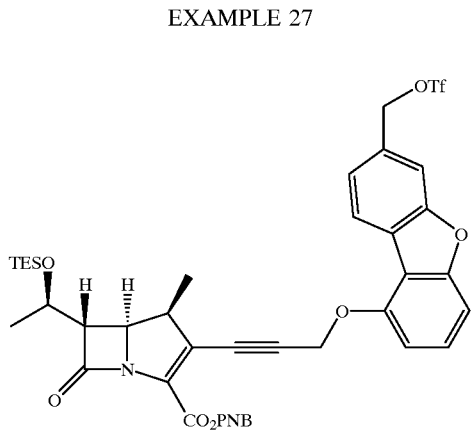

Using the prodecure described in example 7, a stirred solution of 60 mg (0.104 mmoles) of the product obtained in example 26, in 1.0 ml of anhydrous THF, cooled to −20° C., is reacted with 2,6-lutidine (0.013 ml, 0.109 mmoles) and triflic anhydride (0.019 ml, 0.114 mmoles) and used without purification.

EXAMPLE 28

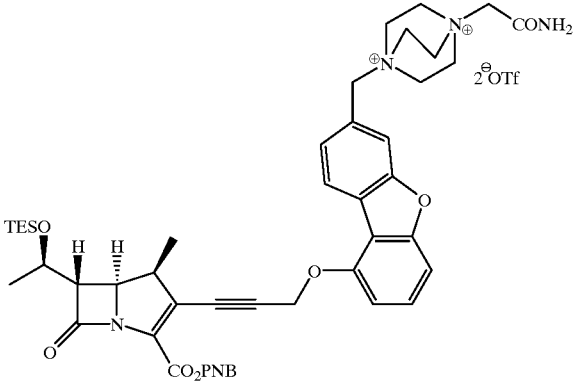

Using the prodecure described in example 8, a stirred solution of 63 mg (0.0747 mmoles) of freshly prepared product obtained from example 27, in 1.0 ml of sieve dried acetonitrile, at ambient temperature, is added 4-carbamoylmethyl-1,4-diazoniabicyclo-{2.2.2}-octyl triflate (24 mg, 0.0747 mmoles). Precipitation from acetone/ether gives the product.

EXAMPLE 29

Using the procedure described in example 9, a stirred solution of 47 mg (0.0416 mmoles) the product obtained in example 28, in 1.0 ml of a 2:1 mixture of THF-H$_2$O, cooled to 0° C., is treated 1.0 N aq. HCl (0.0416 ml, 0.0416 mmoles) and neutralized with 1.0N aq. sodium bicarbonate (0.0416 ml, 0.0416 mmoles). The mixture is hydrogenated using 5% Pt/C (4.7 mg), treated with Macro prep ion exchange resin and desalted using amberchrom CG-161 resin to give after lyophilization the product.

What is claimed is:

1. A compound represented by formula I:

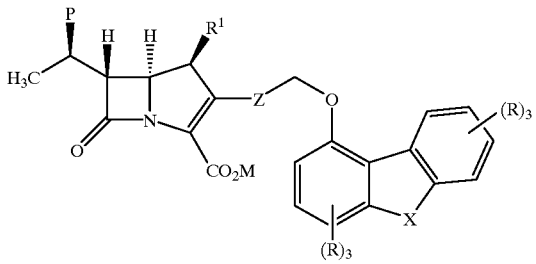

or a pharmaceutically acceptable salt thereof, wherein:

wherein the molecule contains no more than two positive charges balanced by two negatively charged counterions consisting of L⁻ and/or CO$_2$M, wherein CO$_2$M is a carboxylate anion, to provide overall charge neutrality thereto;

$R^1$ represents H or methyl;

CO$_2$M represents a carboxylic acid, a carboxylate anion balanced by a positively charged R group, or a pharmaceutically acceptable ester group;

P represents hydrogen, hydroxyl or F;

X represents CH$_2$, CHR$^a$, C=CHR$^a$, O, S, SO, SO$_2$, CO, COO, OCO, NR$^a$;

Z represents trans-ethenediyl or ethynediyl;

each R is independently selected from: A—(CH$_2$)$_n$—Q, wherein A is O, S or CH$_2$, and n is 0 to 3 when A is CH$_2$, and n is 1 to 3 when A is O or S; —R*; —Q; hydrogen; halo; —CN; —N$_2$; —NR$^a$R$^b$; —OR$^c$; —SR$^c$; —C(O)NR$^a$R$^b$; —C(O)OR$^h$; —S(O)R$^c$; —SO$_2$R$^c$; —SO$_2$NR$^a$R$^b$; —NR$^a$SO$_2$R$^b$; —C(O)R$^a$; —OC(O)R$^a$; —OC(O)NR$^a$R$^b$; —NR$^a$C(O)NR$^b$R$^c$; —NR$^a$CO$_2$R$^b$; —OCO$_2$R$^h$; —NR$^a$C(O)R$^b$; —C$_{1-6}$ straight- or branched-chain alkyl, unsubstituted or substituted with one to four R$^d$ groups; and —C$_{3-7}$ cycloalkyl, unsubstituted or substituted with one to four R$^d$ groups;

each R$^a$, R$^b$ and R$^c$ independently represents hydrogen, —R*, —C$_{1-6}$ straight- or branched-chain alkyl, unsubstituted or substituted with one to four R$^d$ groups, or —C$_{3-7}$ cycloalkyl, unsubstituted or substituted with one to four R$^d$ groups;

each R$^d$ independently represents halo; —CN; —NO$_2$; —NR$^e$R$^f$; —OR$^g$; —SR$^g$; —CONR$^e$R$^f$; —COOR$^g$; —SOR$^g$; —SO$_2$R$^g$; —SO$_2$NR$^e$R$^f$; —NR$^e$SO$_2$R$^f$; —COR$_e$; —NR$_e$COR$^f$; —OCOR$^e$; —OCONR$^e$R$^f$; —NR$^e$CONR$^f$R$^g$; —NR$^e$CO$_2$R$^h$; —OCO$_2$R$^h$; —C(NR$^e$)NR$^f$R$^g$; —NR$^e$C(NH)NR$^f$R$^g$; —NR$^e$C(NR$^f$)R$^g$; —R* or —Q;

R$^e$, R$^f$ and R$^g$ represent hydrogen; —R*; —C$_{1-6}$ straight- or branched-chain alkyl unsubstituted or substituted with one to four R$^i$ groups;

each R$^i$ independently represents halo; —CN; —NO$_2$; phenyl; —NHSO$_2$R$^h$; —OR$^h$, —SR$^h$; —N(R$^h$)$_2$; —N$^+$(R$^h$)$_3$; —C(O)N(R$^h$)$_2$; —SO$_2$N(R$^h$)$_2$; heteroaryl; heteroarylium; —CO$_2$R$^h$; —C(O)R$^h$; —OCOR$^h$; —NHCOR$^h$; guanidinyl; carbaimidoyl or ureido;

each R$^h$ independently represents hydrogen, a —C$_{1-6}$ straight or branched-chain alkyl group, a —C$_3$–C$_6$ cycloalkyl group or phenyl, Q is selected from the group consisting of:

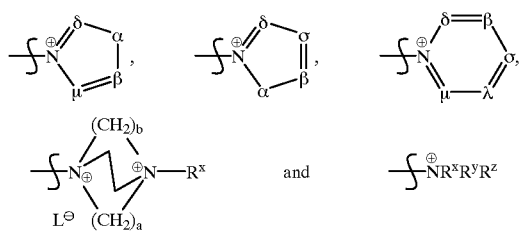

wherein:

a and b are 1, 2 or 3;

L⁻ is a pharmaceutically acceptable counterion and can be present or absent as necessary to maintain appropriate charge balance;

α represents O, S or NR$^s$;

β, δ, λ, μ and σ represent CR$^t$, N or N$^+$R$^s$, provided that no more than one of β, δ, λ, μ and σ is N$^+$R$^s$;

R* is selected from the group consisting of:

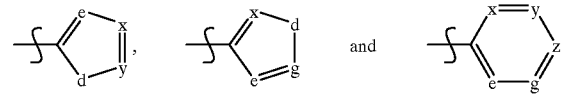

wherein:

d represents O, S or NR$^k$;

e, g, x, y and z represent CR$^m$, N or N$^+$R$^k$, provided that no more than one of e, g, x, y and z in any given structure represents N$^+$R$^k$;

R$^k$ represents hydrogen; —C$_{1-6}$ straight- or branched-chain alkyl, unsubstituted or substituted with one to four R$^i$ groups; or —(CH$_2$)$_n$Q where n=1, 2 or 3 and Q is as previously defined;

each R$^m$ independently represents a member selected from the group consisting of: hydrogen; halo; —CN; —NO$_2$; —NR$^n$R$^o$; —OR$^n$; —SR$^n$; —CONR$^n$R$^o$; —COOR$^h$; —SOR$^n$; —SO$_2$R$^n$; —SO$_2$NR$^n$R$^o$; —NR$^n$SO$_2$R$^o$; —COR$^n$; —NR$^n$COR$^o$; —OCOR$^n$; —OCONR$^n$R$^o$; —NR$^n$CO$_2$R$^h$; —NR$^n$CONR$^o$R$^h$; —OCO$_2$R$^h$; —CNR$^n$NR$^o$R$^h$; —NR$^n$CNHNR$^o$R$^h$; —NR$^n$C(NR$^o$)R$^h$; —C$_{1-6}$ straight- or branched-chain alkyl, unsubstituted or substituted with one to four R$^i$ groups; —C$_{3-7}$ cycloalkyl, unsubstituted or substituted with one to four R$^i$ groups; and —(CH$_2$)$_n$Q where n and Q are as defined above;

R$^n$ and R$^o$ represent hydrogen, phenyl; —C$_{1-6}$ straight- or branched-chain alkyl unsubstituted or substituted with one to four R$^i$ groups;

each R$^s$ independently represents hydrogen; phenyl or —C$_{1-6}$ straight- or branched-chain alkyl, unsubstituted or substituted with one to four R$^i$ groups;

each R$^t$ independently represents hydrogen; halo; phenyl; —CN; —NO$_2$; —NR$^u$R$^v$; —OR$^u$; —SR$^u$; —CONR$^u$R$^v$; —COOR$^h$; —SOR$^u$; —SO$_2$R$^u$; —SO$_2$NR$^u$R$^v$; —NR$^u$SO$_2$R$^v$; —COR$^u$; —NR$^u$COR$^v$; —OCOR$^u$; —OCONR$^u$R$^v$; —NR$^u$CO$_2$R$^v$; —NR$^u$CONR$^v$R$^w$; —OCO$_2$R$^v$; —C$_{1-6}$ straight- or branched-chain alkyl, unsubstituted or substituted with one to four R$^i$ groups;

R$^u$ and R$^v$ represent hydrogen or —C$_{1-6}$ straight- or branched-chain alkyl, unsubstituted or substituted with one to four R$^i$ groups;

each $R^w$ independently represents hydrogen; —$C_{1-6}$ straight- or branched-chain alkyl, unsubstituted or substituted with one to four $R^i$ groups; $C_{3-6}$ cycloalkyl optionally substituted with one to four $R^i$ groups; phenyl optionally substituted with one to four $R^i$ groups, or heteroaryl optionally substituted with 1–4 $R^i$ groups;

$R^x$ represents hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, or a phenyl or heteroaryl group which is in turn optionally substituted with from one to four $R^i$ groups or with one to two $C_{1-3}$ straight- or branched-chain alkyl groups, said alkyl groups being unsubstituted or substituted with one to four $R^i$ groups; and $R^y$ and $R^z$ represent hydrogen; phenyl; —$C_{1-6}$ straight or branched chain alkyl, unsubstituted or substituted with one to four $R^i$ groups, and optionally interrupted by O, S, $NR^w$, $N^+R^hR^w$ or —C(O)—.

2. A compound in accordance with claim 1 wherein $CO_2M$ represents a carboxylate anion.

3. A compound in accordance with claim 1 wherein one R represents a group which contains a positively charged moiety, and the remaining R groups are selected from hydrogen and $C_{1-6}$ straight or branched chain alkyl, unsubstituted or substituted with one to four $R^d$ groups.

4. A compound in accordance with claim 3 wherein one R represents a group containing a positively charged moiety and the remaining R groups are hydrogen.

5. A compound in accordance with claim 1 wherein the R groups contain from 1–2 positive charges.

6. A compound in accordance with claim 5 wherein the R groups contain two positive charges, balanced by a carboxylate anion and a counterionL.

7. A compound in accordance with claim 1 wherein one R group represents a —$C_{1-6}$ straight or branched chain alkyl group, substituted with one to four $R^d$ groups, wherein one $R^d$ group represents —R* or Q.

8. A compound in accordance with claim 1 wherein Q is selected from the group consisting of:

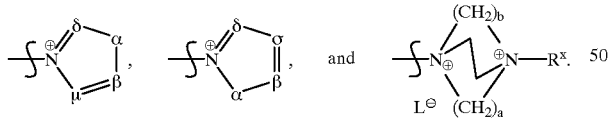

9. A compound in accordance with claim 8 wherein Q represents:

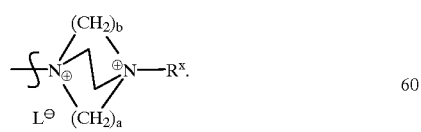

L⁻, a and b are as originally defined, and $R^x$ represent a member selected from the group consisting of: hydrogen or a $C_{1-8}$ straight- or branched-chain alkyl, optionally interrupted or terminated by one or two of O, S, SO, $S_2$, $NR^w$, $N^+R^hR^w$, or —C(O)—, ,said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, phenyl, or heteroaryl, said phenyl and heteroaryl being optionally substituted with from one to four $R^i$ groups or with one to two $C_{1-3}$ straight- or branched-chain alkyl groups, said alkyl groups being unsubstituted or substituted with one to four $R^i$ groups, and $R^h$, $R^i$ and $R^w$ are as originally defined.

10. A compound in accordance with claim 1 wherein Q represents —$N^+R^xR^yR^z$, wherein $R^x$, $R^y$ and $R^z$ are as originally defined.

11. A compound in accordance with claim 1 wherein one R* group is present and is selected from:

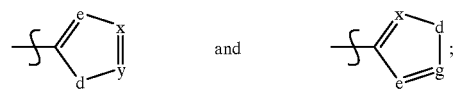

d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

12. A compound in accordance with claim 1 wherein:

$CO_2M$ represents a carboxylate anion;

one R group which is attached to the condensed biaryl platform contains at least one positively charged moiety, and the remaining R groups are selected from hydrogen and $C_{1-6}$ straight or branched chain alkyl, unsubstituted or substituted with one to four $R^d$ groups.

Rd is as originally defined;

$R^h$ represents hydrogen or a $C_{1-6}$ straight or branched chain alkyl group;

Q is selected from the group consisting of:

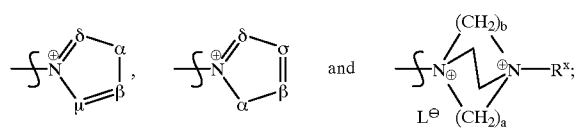

wherein L⁻ is as originally defined; a and b represent 2, and $R^x$ represents a member selected from the group consisting of: hydrogen or a $C_{1-8}$ straight- or branched-chain alkyl, optionally interrupted or terminated by one or two of O, S, SO, $S_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, phenyl, or heteroaryl, said phenyl and heteroaryl being optionally substituted with from one to four $R^i$ groups or with one to two $C_{1-3}$ straight- or branched-chain alkyl groups, said alkyl groups being unsubstituted or substituted with one to four $R^i$ groups;

R* is selected from:

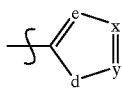 and 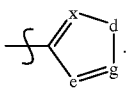

wherein d represents $NR^k$; $R^k$ represents $-C_{1-6}$ straight or branched chain alkyl; and e, g, x and y represent $CR^m$ or $N^+R^k$, with $R^k$ as defined above and $R^m$ representing hydrogen.

13. A compound in accordance with claim 1 wherein R is $A-(CH_2)_n-Q$, wherein A is O, S or $CH_2$ and n is 1–3 and Q is as originally defined.

14. A compound in accordance with claim 1 wherein Z is trans-CH=CH.

15. A compound in accordance with claim 1 wherein Z is $-C \equiv C-$.

16. A compound in accordance with claim 1 wherein X is $CHR^a$, CO, O or S.

17. A compound according to claim 1 represented by structural formula Ia:

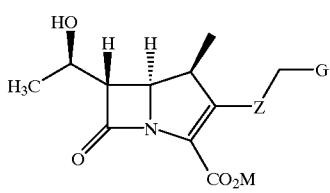

wherein G is:

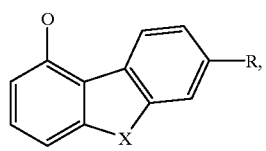

1

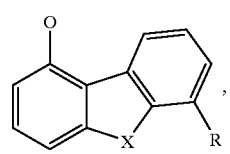

2

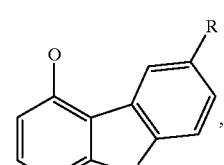

3

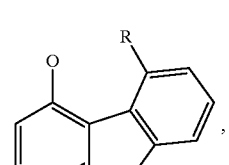

4

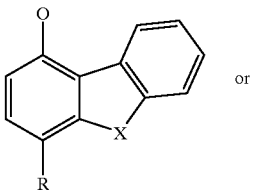

5 or

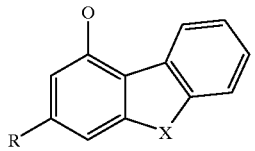

6 wherein

Z is as originally described;

$CO_2M$ represents a carboxylate anion;

X represents $CH_2$, $CHR^a$, CO, O, S, or $NR^a$;

one R group contains at least one positively charged moiety, and the remaining R groups are selected from hydrogen and $C_{1-6}$ straight or branched chain alkyl, unsubstituted or substituted with one to four $R^d$ groups;

Rd is as originally defined;

$R^h$ represents hydrogen or a $C_{1-6}$ straight or branched chain alkyl group;

Q is selected from the group consisting of:

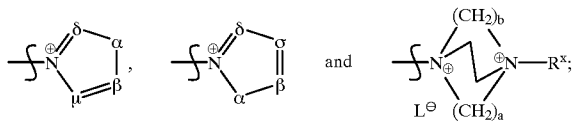

wherein $L^-$, a and b are as originally defined, and $R^x$ represents a member selected from the group consisting of: hydrogen or a $C_{1-8}$ straight- or branched-chain alkyl, optionally interrupted or terminated by one or two of O, S, SO, $S_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl or heteroaryl group being optionally substituted with from one to four $R^i$ groups or with one to two $C_{1-3}$ straight- or branched-chain alkyl groups, said alkyl groups being unsubstituted or substituted with one to four $R^i$ groups;

R* is selected from:

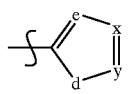 and 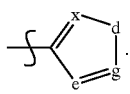

wherein d represents $NR^k$; $R^k$ represents $-C_{1-6}$ straight or branched chain alkyl; and e, g, x and y represent $CR^m$ or $N^+R^k$, with $R^k$ as defined above and $R^m$ representing hydrogen.

18. A compound according to claim 17 wherein G is 1, 2 or 5.

19. A compound according to claim 17 wherein:

R represents

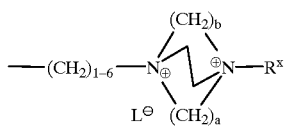

and $R^x$, a, b and $L^-$ are as originally defined.

20. A compound according to claim 1 represented by structural formula Ib:

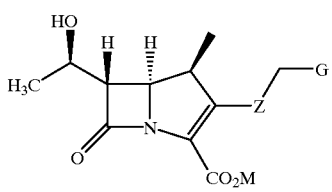

wherein G is:

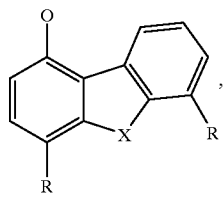

7

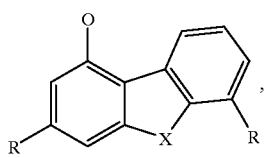

8

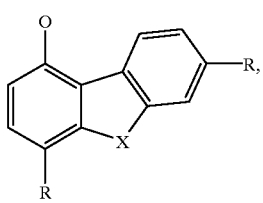

9

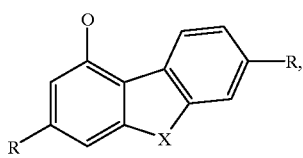

10

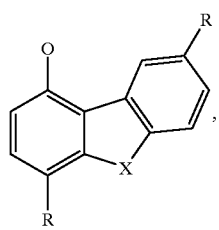

11

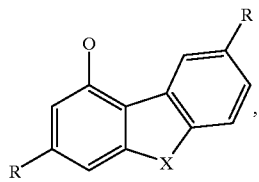

12

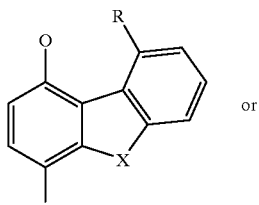

13

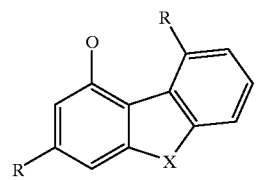

14 or a pharmaceutically acceptable salt thereof, wherein:

Z is as originally described;

$CO_2M$ represents a carboxylate anion;

one R group contains a positively charged moiety, and the other R group is selected from hydrogen and $C_{1-6}$ straight or branched chain alkyl, unsubstituted or substituted with one to four $R^d$ groups;

$R^d$ is as originally defined;

Q is selected from the group consisting of:

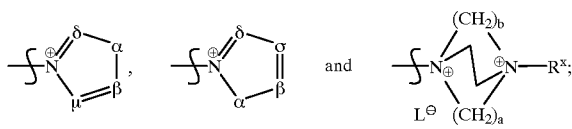

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, $C(O)NR^hR^w$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight- or branched-chain alkyl groups, said alkyl groups being unsubstituted or substituted with one to four $R^i$ groups;

$R^h$ represents hydrogen or a $C_{1-6}$ straight or branched chain alkyl group;

$R^w$ is as originally defined;

R* is selected from:

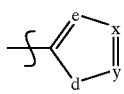 and 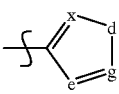

wherein d represents $NR^k$; $R^k$ represents $—C_{1-6}$ straight or branched chain alkyl; and e, g, x and y represent $CR^m$ or $N^+R^k$, with $R^k$ as defined above and $R^m$ representing hydrogen.

21. A compound according to claim 20 where G is 7 or 8.

22. A compound according to claim 20 wherein:

R represents

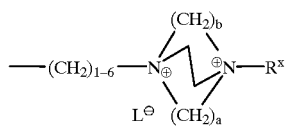

and $R^x$, a, b and $L^-$ are as originally defined.

23. A compound according to claim 1 represented by formula Ic:

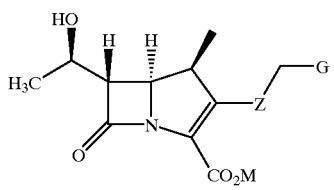

wherein G is:

1

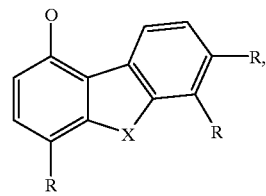

2

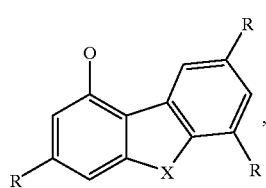

3

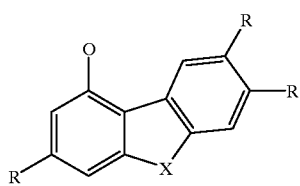

4

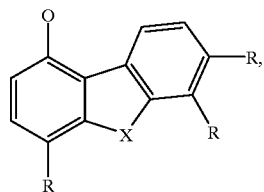

5

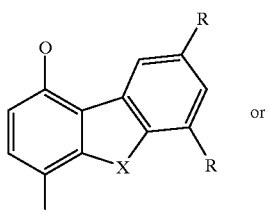 or

6

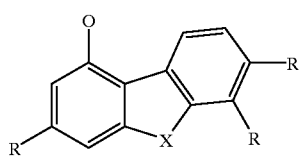

or a pharmaceutically acceptable salt thereof, wherein:

Z is as originally described;

$C_2M$ represents a carboxylate anion;

one R group is attached to the condensed biaryl platform which contains a positively charged moiety, and the other R groups are selected from hydrogen, halo and $C_{1-6}$ straight or branched chain alkyl, unsubstituted or substituted with one to four $R^d$ groups;

$R^d$ is as originally defined;

Q is selected from the group consisting of:

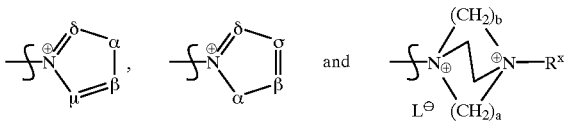

wherein $L^-$, a and b are as originally defined, and $R^x$ represents a member selected from the group consisting of: hydrogen or a $C_{1-8}$ straight- or branched-chain alkyl, optionally interrupted by one or two of O, S, SO, $S_2$, $NR^w$, $N^+R^hR^w$, or $—C(O)—$, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, $—C(O)—R^w$, $C(O)NR^{Rw}$, $SO_2NR^hR^w$, $CO_2R^w$, $OC(O)R^w$, $OC(O)NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;

$R^h$ represents hydrogen or a $C_{1-6}$ straight or branched chain alkyl group;

$R^w$ is as originally defined;

R* is selected from:

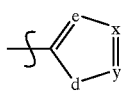 and 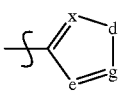

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

24. A compound according to claim 1 which is represented by structural formula Id:

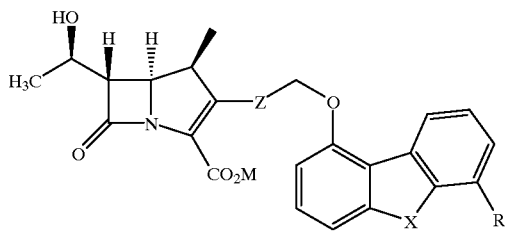

Id or a pharmaceutically acceptable salt thereof, wherein:
Z is as originally described;
R contains a positively charged moiety selected from the group consisting of: —R*, Q, A—$(CH_2)_n$—Q, and a $C_{1-6}$ straight or branched alkyl chain substituted with one $R^d$ group, wherein A is $CH_2$ and n is 2, or 3;
$R^d$ is independently selected —R* or Q;
Q is selected from the group consisting of:

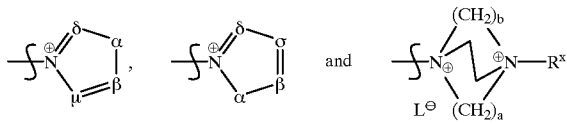

wherein L⁻, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;
R* is selected from:

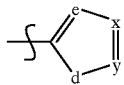 and 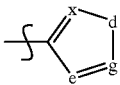

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

25. A compound according to claim 1 which is represented by structural formula Ie:

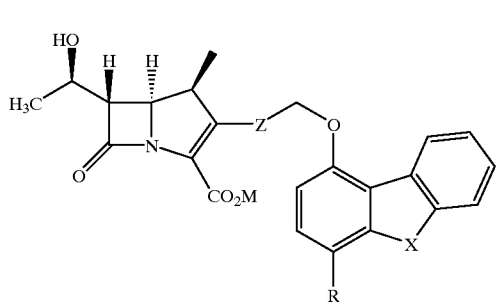

Ie or a pharmaceutically acceptable salt thereof, wherein:

R contains a positively charged moiety selected from the group consisting of: —R*, Q, A—$(CH_2)_n$—Q, and a $C_{1-6}$ straight or branched alkyl chain substituted with one $R^d$ group, wherein A is selected from the group consisting of O, S and $CH_2$, and n is 1 to 3;
$R^d$ is independently selected —R* or Q;
Q is selected from the group consisting of:

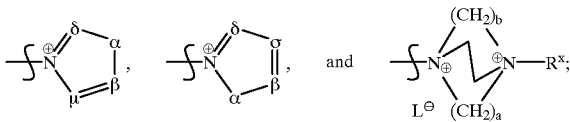

wherein L⁻, a and b are as originally defined, and $R^x$ represents a member selected from the group consisting of: hydrogen or a $C_{1-8}$ straight- or branched-chain alkyl, optionally interrupted by one or two of O, S, SO, $SO_2$, $NR^w$, $N^+R^hR^w$, or —C(O)—, said chain being unsubstituted or substituted with one to four of halo, CN, $NO_2$, $OR^w$, $SR^w$, $SOR^w$, $SO_2R^w$, $NR^hR^w$, $N^+(R^h)_2R^w$, —C(O)—$R^w$, C(O)$NR^hR^w$, $SO_2NR^hR^w$, $CO_2R^w$, OC(O)$R^w$, OC(O)$NR^hR^w$, $NR^hC(O)R^w$, $NR^hC(O)NR^hR^w$, phenyl or heteroaryl, said phenyl and heteroaryl group being optionally substituted with from one to four $R^i$ groups or with one to two $C_{1-3}$ straight or branched chain alkyl groups, said alkyl groups being unsubstituted or substituted with one to four $R^i$ groups;
R* is selected from:

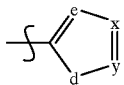 and 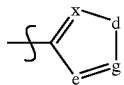

wherein d represents $NR^k$; $R^k$ represents —$C_{1-6}$ straight or branched chain alkyl; and e, g, x and y represent $CR^m$ or $N^+R^k$, with $R^k$ as defined above and $R^m$ representing hydrogen.

26. A pharmaceutical composition comprised of a compound in accordance with claim 1 in combination with a pharmaceutically acceptable carrier.

27. A compound which is:
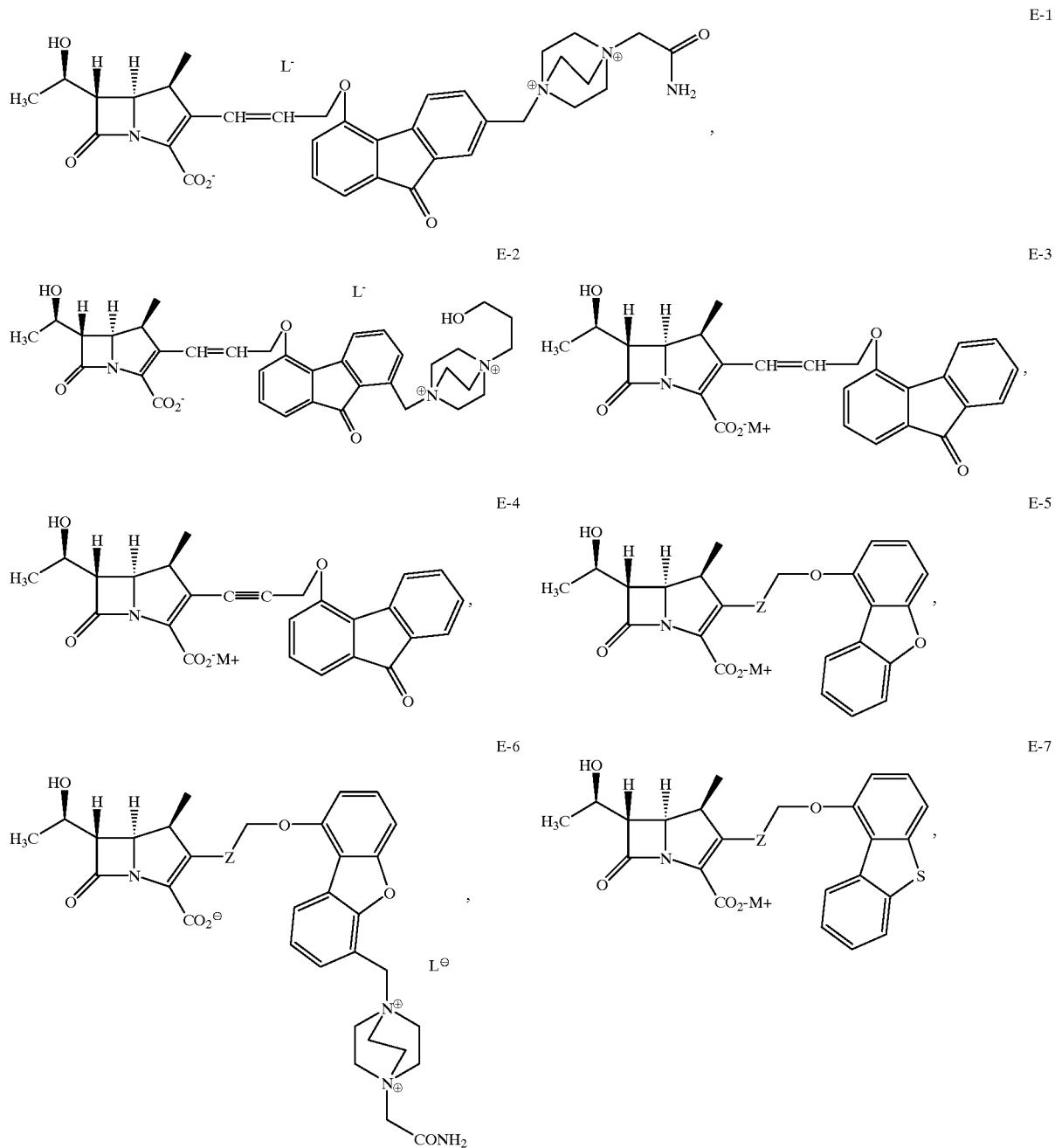

-continued
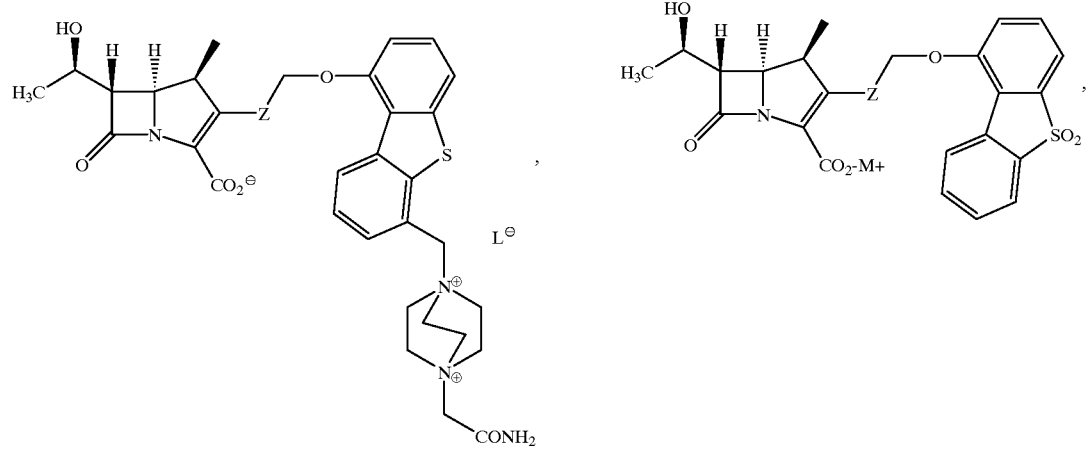
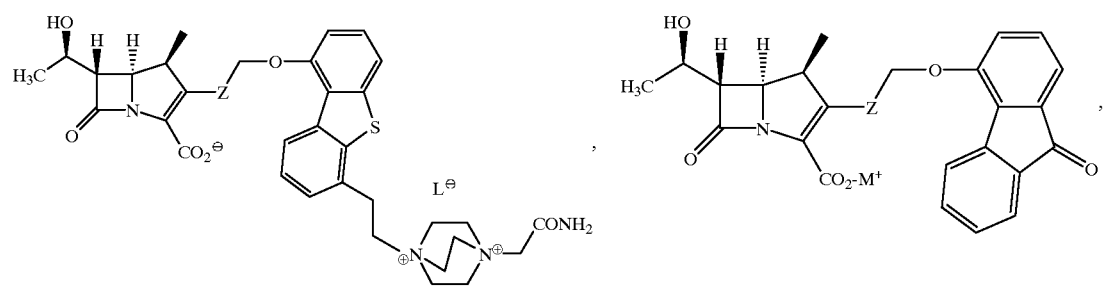
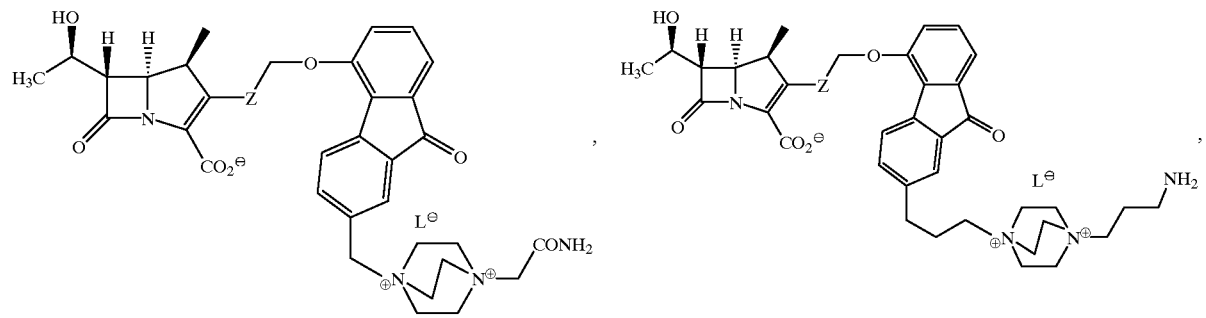
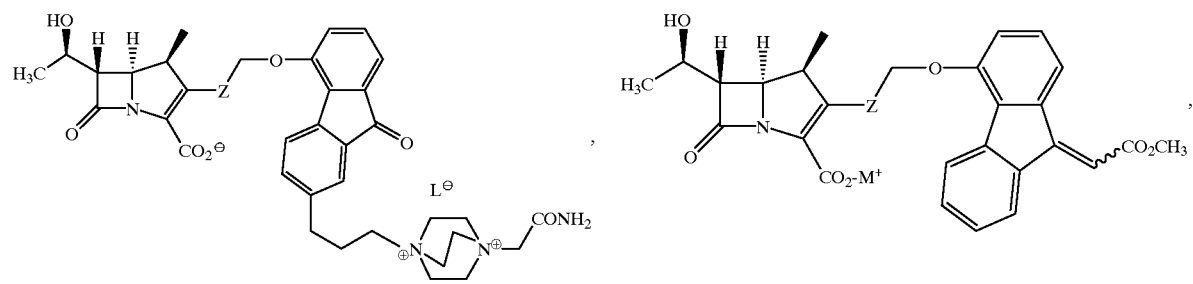

-continued
E-16
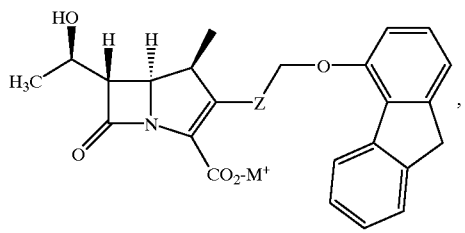
E-17
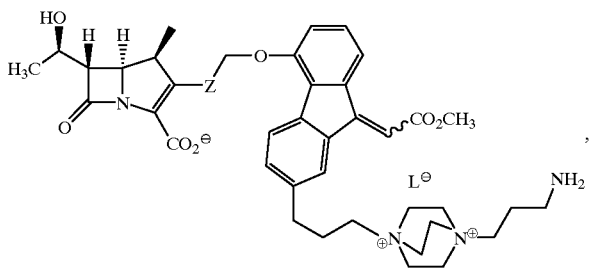
E-18
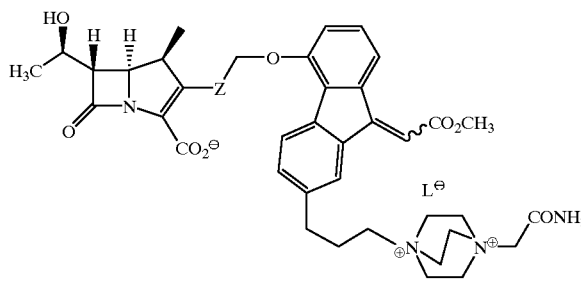
E-19
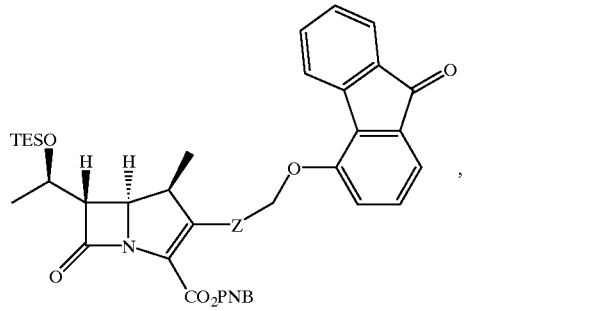
E-20
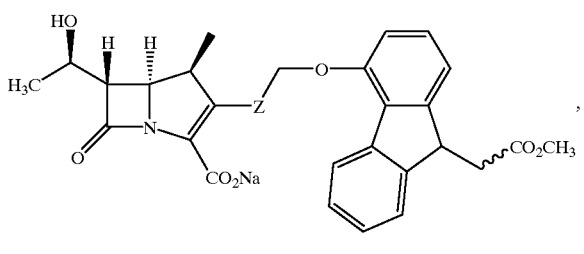
E-21
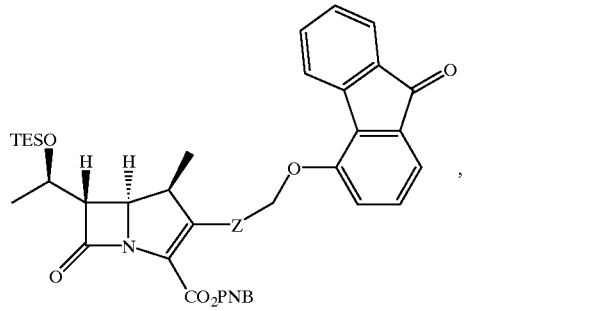
E-22
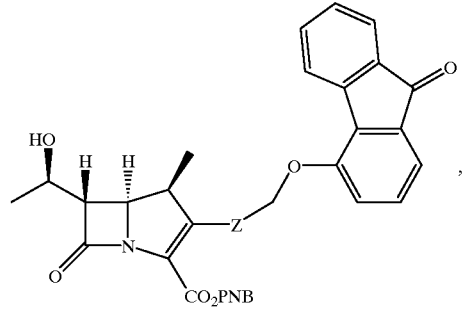
E-23
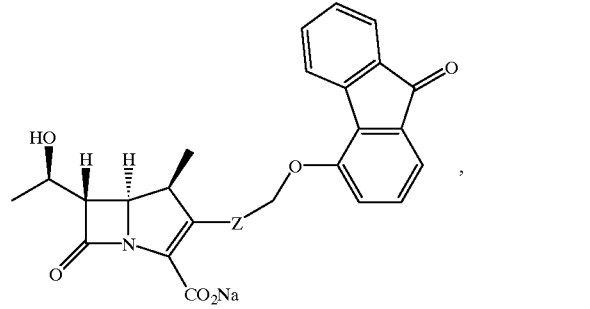

E-24
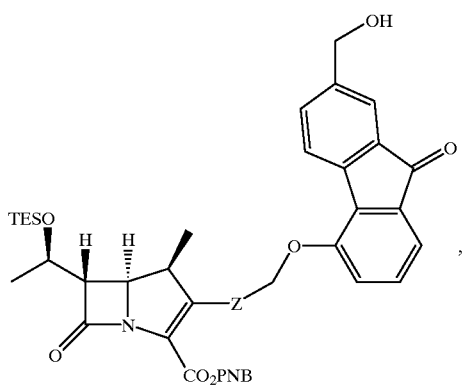

E-25
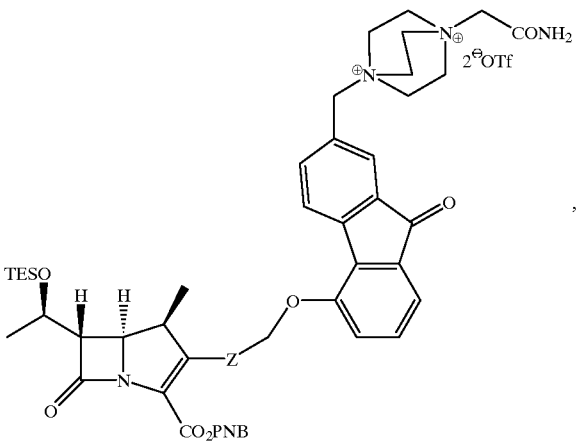

E-26
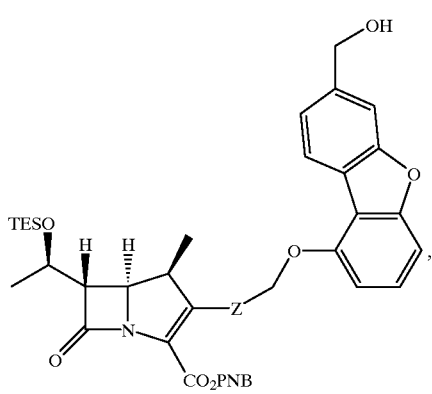

E-27
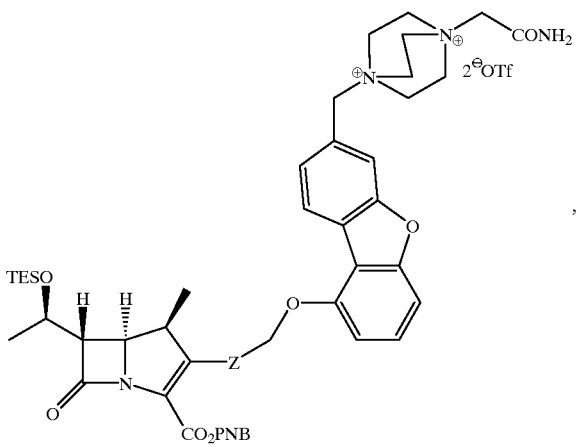

E-28
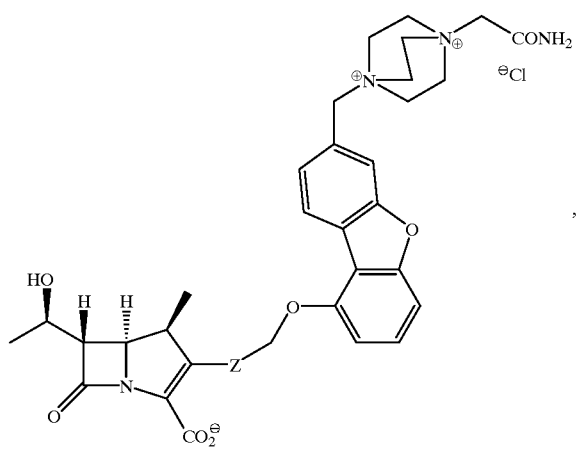

or the pharmaceutically acceptable salts thereof, wherein TES is triethylsilyl, L– is a pharmaceutically acceptable counterion, PNB is p-nitrobenzyl, OTf is triflate and M+ is a metal cation.

28. A method of treating or preventing a bacterial infection in a mammalian patient in need thereof, comprising administering to said patient an effective amount of a compound of claim 1.

* * * * *